US008815824B2

(12) United States Patent
Neufeld

(10) Patent No.: US 8,815,824 B2
(45) Date of Patent: Aug. 26, 2014

(54) COMPOSITIONS AND METHODS FOR TREATING TUMORS, FIBROSIS, AND PULMONARY ALVEOLAR PROTEINOSIS

(75) Inventor: Gera Neufeld, Haifa (IL)

(73) Assignee: Technion Research & Development Foundation Ltd. (IL)

( * ) Notice: Subject to any disclaimer, the term of this patent is extended or adjusted under 35 U.S.C. 154(b) by 0 days.

(21) Appl. No.: 13/619,511

(22) Filed: Sep. 14, 2012

(65) Prior Publication Data

US 2013/0022617 A1   Jan. 24, 2013

Related U.S. Application Data

(62) Division of application No. 12/669,035, filed as application No. PCT/IL2008/000985 on Jul. 15, 2008, now Pat. No. 8,389,709.

(30) Foreign Application Priority Data

Jul. 15, 2007  (IL) .......................................... 184627

(51) Int. Cl.
*A61K 48/00* (2006.01)
*C07H 21/02* (2006.01)
*C07H 21/04* (2006.01)

(52) U.S. Cl.
USPC ............................ 514/44; 536/23.1; 536/24.5

(58) Field of Classification Search
CPC ........... C12N 15/1137; C12N 2310/14; C12N 2310/531
See application file for complete search history.

(56) References Cited

U.S. PATENT DOCUMENTS

| 5,721,138 | A  | 2/1998  | Lawn |
| 6,300,092 | B1 | 10/2001 | Khodadoust et al. |
| 8,163,494 | B2 | 4/2012  | Neufeld et al. |
| 8,168,180 | B2 | 5/2012  | Neufeld et al. |
| 2002/0123476 | A1 | 9/2002 | Emanuele et al. |
| 2002/0128218 | A1 | 9/2002 | Emanuele et al. |
| 2003/0017068 | A1 | 1/2003 | Larrain et al. |
| 2003/0096980 | A1 | 5/2003 | Froehler et al. |
| 2003/0114410 | A1 | 6/2003 | Neufeld et al. |
| 2006/0127402 | A1 | 6/2006 | Neufeld et al. |
| 2007/0021365 | A1 | 1/2007 | Erler et al. |
| 2010/0119515 | A1 | 5/2010 | Neufeld et al. |
| 2010/0317721 | A1 | 12/2010 | Neufeld |
| 2012/0165398 | A1 | 6/2012 | Neufeld et al. |
| 2012/0202206 | A1 | 8/2012 | Neufeld et al. |

FOREIGN PATENT DOCUMENTS

| EP | 2 078 531 | 7/2009 |
| EP | 1 315 519 | 12/2010 |
| EP | 2179040 B1 | 6/2013 |
| EP | 2359854 B1 | 10/2013 |
| WO | WO-89/12060 | 12/1989 |
| WO | WO-92/20702 | 11/1992 |
| WO | WO-98/06830 | 2/1998 |
| WO | WO-01/83702 | 11/2001 |
| WO | WO-02/11667 | 2/2002 |
| WO | WO-2004/047720 | 6/2004 |
| WO | WO-2004/061423 | 7/2004 |
| WO | WO-2006/128740 | 7/2006 |
| WO | WO-2007/126457 | 11/2007 |
| WO | WO-2009/010974 | 1/2009 |

OTHER PUBLICATIONS

Office Action for Israeli Patent Application No. 222541 mailed Mar. 12, 2013.
Office Action for Israeli Patent Application No. 222542 mailed Mar. 12, 2013.
Office Action for Israeli Patent Application No. 222543 mailed Mar. 13, 2013.
Office Action for Israeli Patent Application No. 222544 mailed Mar. 13, 2013.
Office Action for U.S. Appl. No. 12/669,035, mailed Jun. 24, 2011.
Office Action for U.S. Appl. No. 12/669,035, mailed Nov. 15, 2011.
Office Action for U.S. Appl. No. 12/669,035, mailed Mar. 13, 2012.
Notice of Allowance for U.S. Appl. No. 12/669,035, mailed Jun. 27, 2012.
Notice of Allowance for U.S. Appl. No. 12/669,035, mailed Oct. 19, 2012.
Akiri et al., "Lysyl Oxidase-Related Protein-1 Promotes Tumor Fibrosis and Tumor Progression in Vivo," Cancer Research (2003) 63(7):1657-1666.
Aoki et al., Biochem. Biophys. Res. Commun. (1997) 231:540-545.
Beal et al., Science (1992) 251:1360-1363.
Bernstein, Nature (2001) 409:363-366.
Besch et al., J. Biol. Chem. (2002) 277:32473-32479.
Brantl, Biochem. Biophys. Act. (2002) 1575:15-25.
Breaker et al., Chemistry and Biology (1995) 2:655-660.
Brennan et al., Cancer: Principles and Practice of Oncology, Fourth Edition, pp. 849-882, Philadelphia, PA: J.B. Lippincott Co. (1993).
Bronson et al., "LOXL Null Mice Demonstrate Selective Dentate Structural Changes but Maintain Dentate Granule Cell and CA1 Pyramidal Cell Potentiation in the Hippocampus," Neuroscience Letters (2005) 390:118-122.
Brooks et al., "Integrin $\alpha_v\beta_3$ Antagonists Promote Tumor Regression by Inducing Apoptosis of Angiogenic Blood Vessels," Cell (1994) 79:1157-1164.
Brooks et al., "Disruption of Angiogenesis by PEX, a Noncatalytic Metalloproteinase Fragment with Integrin Binding Activity," Cell (1998) 92:391-400.
Brown et al., Biochemistry (1994) 33:13918-13927.
Brummelkamp et al., "A System for Stable Expression of Short Interfering RNAs in Mammalian Cells," Science (2002) 296:550-553.

(Continued)

*Primary Examiner* — Amy Bowman
(74) *Attorney, Agent, or Firm* — Cooley LLP

(57) ABSTRACT

The present disclosure provides pharmaceutical compositions and methods useful for modulating angiogenesis and for inhibiting metastasis, tumors, pulmonary alveolar proteinosis, and fibrosis in a mammalian tissue. Pharmaceutical compositions and methods include inhibitors of LOXL2 expression and activity, such as shRNA targeting LOXL2.

12 Claims, 11 Drawing Sheets

(56) References Cited

OTHER PUBLICATIONS

Carbone et al., Nucl. Acid Res. (2003) 31:833-843.
Carthew, "Gene Silencing by Double-Stranded RNA," Current Opinion Cell Biology (2001) 13:244-248.
Colpaert et al., Am. J. Surg. Pathol (2001) 25:1557.
Cook et al., Anti-Cancer Drug Design 6:585 (1991).
Cooney et al., Science (1988) 241:456-459.
Csiszar, "Lysyl Oxidases: A Novel Multifunctional Amine Oxidase Family," Progress in Nucleic Acid Research and Molecular Biology (2001) 70:1-32.
Cullen, Nat. Immunol. (2002) 3:597-599.
Database EMBL, Sequence 15133 from Patent WO2004061423, GenBank accession No. FB530075.1, Oct. 28, 2008.
Devroe et al., BMC Biotechnol. (2002) 2:15.
Duffy et al., Breast Cancer Res. (2000) 2:252-257.
Elbashir et al., Genes Dev. (2001) 15:188-200.
Ellenrieder et al., Int. J. Cancer (2000) 85:14-20.
Fong et al., "Lysyl Oxidase-Like 2 Expression is Increased in Colon and Esophageal Tumors and Associated with Less Differentiated Colon Tumors," Genes, Chromosomes & Cancer (2007) 46(7):644-655.
Gengrinovitch et al., J. Biol. Chem. (1995) 270-15059-15065.
Gewirtz, "Oligonucleotide Therapeutics: Clothing the Emperor," Current Opinion Molecular Therapeutics (1999) 1:297-306.
Gorough et al., "Selective Upregulation and Amplification of the Lysyl Oxidase Like-4 (LOXL4) Gene in Head and Neck Squamous Cell Carcinoma," Journal of Pathology (2007) 212:74-82.
Gupta et al., J. Cell Biol. (1994) 127:1121-1127.
Hammond et al., Nat. Rev. Gen. (2001) 2:110-119.
Hansell et al., "Selective Binding of Platelet Factor 4 to Regions of Active Angiogenesis in Vivo," American Journal of Physiology (1995) 38:H829-H836.
Harris et al., "Breast Cancer Angiogenesis—New Approaches to Therapy via Antiangiogenesis, Hypoxic Activated Drugs, and Vascular Targeting," Breast Cancer Research and Treatment (1996) 38:97-108.
Hasebe et al., Pathology International 50 (2000) 263:272.
Hein, "Lysyl Oxidases: Expression in the Fetal Membranes and Placenta," Placenta (2001) 22(1):49-57.
Hoheneste et al., Nat. Struct. Biol. (1999) 6:228-232.
Holmlund et al., "Toward Antisense Oligonucleotide Therapy for Cancer: ISIS Compounds in Clinical Development," Current Opinion in Molecular Therapeutics (1999) 1:372-385.
Hornstra et al., "Lysyl Oxidase is Required for Vascular and Diaphragmatic Development in Mice," Journal of Biological Chemistry (2003) 278:14387-14393.
Hutvagner et al., Curr. Opin. Genet. Dev. (2002) 12:225-232.
International Search Report for International Patent Application No. PCT/IL2008/00985, mailed Oct. 7, 2009, 6 pages.
Itoh et al., 2002, Abstract 409, Ann Meeting Am. Soc. Gen. Ther. www.asgt.org.
Jacque et al., "Modulation of HIV-1 Replication by RNA Interference," Nature (2002) 418:435-438.
Jiang et al., "Selective Silencing of Viral Gene Expression in HPV-Positive Human Cervical Carcinoma Cells Treated with siRNA, a Primer of RNA Interference," Oncogene (2002) 21:6041-6048.
Jourdan Le-Saux et al., "Lysyl Oxidase cDNA of Myofibroblast from Mouse Fibrotic Liver," Biochemical and Biophysical Research Communications (1994) 199:587-592.
Kagan et al., "Expression of Lysyl Oxidase from cDNA Constructs in Mammalian Calls: the Propeptide Region is Not Essential to the Folding and Secretion of the Functional Enzyme," Journal of Cellular Biochemistry (1995) 59:329-338.
Kagan et al., "Lysyl Oxidase: Properties, Specificity, and Biological Roles Inside and Outside of the Cell," Journal of Cellular Biochemistry (2003) 88:660-672.
Kagan, "Lysyl Oxidase: Mechanism, Regulation and Relationship to Liver Fibrosis," Pathology, Research and Practice (1994) 190:910-919.
Khachigian, Curr. Opin. Mol. Ther. (2002) 4:119-121.

Kim et al., J. Biol. Chem. (2003) 278:52071-52074.
Kim et al., "Coexpression of the Lysyl Oxidase-Like Gene (LOXL) and the Gene Encoding Type III Procollagen in Induced Liver Fibrosis," Journal of Cellular Biochemistry (1999) 72:181-188.
Kirschmann et al., "A Molecular Role for Lysyl Oxidase in Breast Cancer Invasion," Cancer Research (2002) 62:4478-4483.
Kirschmann et al., "Differentially Expressed Genes Associated with the Metastatic Phenotype in Breast Cancer," Breast Cancer Research and Treatment (1999) 55(2):127-136.
Klauber et al., "Inhibition of Angiogenesis and Breast Cancer in Mice by the Microtubule Inhibitors 2-Methoxyestradiol and Taxol," Cancer Research (1997) 57:81-86.
Kronenwett et al., Blood (1998) 91:852-862.
Lavigne et al., Biochem. Biophys. Res. Commun. 91997) 237:566-571.
Levene, "Possibilities for the Therapeutic Control of Fibrosis," The British Journal of Dermatology (1985) 112(3):363-371.
Luft, J. Mol. Med. (1998) 76:75-76.
Maher III et al., Science (1989) 245:725-730.
Maione et al., Science (1990) 247:77-79.
Matveeva et al., "Prediction of Antisense Oligonucleotide Efficacy by in Vitro Methods," Nature Biotechnology (1998) 16:1374-1375.
McCaffrey et al., "RNA Interference in Adult Mice," Nature (2002) 418:38-39.
Miyagishi et al., "U6 Promoter-Driven siRNAs with Four Uridine 3' Overhangs Efficiently Suppress Targeted Gene Expression in Mammalian Cells," Nature Biotechnology (2002) 20:497-500.
Molnar et al., "Structural and Functional Diversity of Lysyl Oxidase and the LOX-Like Proteins," Biochimica et Biophysica Acta (2003) 1647:220-224.
Molnar et al., Biochimica Biophysica Acta (2003) 1647:220-224.
Moser et al., Science (1987) 238:645-630.
Murawaki et al., "Serum Lysyl Oxidase Activity in Chronic Liver Disease in Comparison with Serum Levels of Prolyl Hydroxylase and Laminin," Hepatology (1991) 14:1167-1173.
Neufeld et al., FASEB J. (1999) 13:9-22.
Neufeld et al., The Cytokine Reference: A compendium of cytokines and other mediators of host defence (oppenheim, J.J. and Feldman, M. eds) Academic Press (2000).
Nishimura et al., Virchows Arch. (1998) 433:517-522.
O'Reilly et al., "Endostatin: An Endogenous Inhibitor of Angiogenesis and Tumor Growth," Cell (1997) 88:277-285.
O'Reilly et al., "Angiostatin Induces and Sustains Dormancy of Human Primary Tumors in Mice," Nature Medicine (1996) 2:689-692.
Paddison et al., "Short Hairpin RNAs (shRNAs) Induce Sequence-Specific Silencing in Mammalian Cells," Genes & Development (2002) 16:948-958.
Partial European Search Report for EP 12173418.0, mailed Oct. 12, 2012, 6 pages.
Patent Examination Report for AU 2008277263, issued Nov. 1, 2012, 3 pages.
Paul et al., "Effective Expression of Small Interfering RNA in Human Cells," Nature Biotechnology (2002) 20:505-508.
Peinado et al., "A Molecular Role for Lysyl Oxidase-Like 2 Enzyme in Snail Regulation and Tumor Progression," The EMBO Journal (2005) 24(19):3446-3458.
Puri et al., J. Biol. Chem. (2001) 276:28991-28998.
Rabinovitz, "Angiogenesis and its Inhibition: The Copper Connection," Journal of the National Cancer Institute (1999) 91:1689-1690.
Rajur et al., Bioconjug. Chem. (1997) 8:935-940.
Reiser et al., "Enzymatic and Nonenzymatic Cross-Linking of Collagen and Elastin," The FASEB Journal (1992) 6:2439-2449.
Reither et al., BMC Biochem, Sep. 12, 2002, Epub.
Saito et al., "Regulation of a Novel Gene Encoding a Lysyl Oxidase-Related Protein in Cellular Adhesion and Senescence," Journal of Biological Chemistry (1997) 272(13):8157-8160.
Sasaki et al., "Mac-2 Binding Protein is a Cell-Adhesive Protein of the Extracellular Matrix which Self-Assembles into Ring-Line Structures and Binds β1 Integrins, Collagens and Fibronectin," The EMBO Journal (1998) 17:1606-1613.

(56) References Cited

OTHER PUBLICATIONS

Schlaeger et al., "Uniform Vascular-Endothelial-Cell-Specific Gene Expression in Both Embryonic and Adult Transgenic Mice," Proceedings of the National Academy of Sciences of the United States of America (1997) 94:3058-3063.
Schuppan et al., Semin. Liver Dis. (2001) 21:351-372.
Seidman et al., J. Clin. Invest. (2003) 112:487-494.
Sharp, Genes Dev. (2001) 15:485-490.
Siegel et al., "Biochemical and Immunochemical Study of Lysyl Oxidase in Experimental Hepatic Fibrosis in the Rat," Proceedings of the National Academy of Sciences of the United States of America (1978) 75:2945-2949.
Stamenkovic, Semin. Cancer Biol. (2000) 10:415-433.
Swada et al., Int. J. Oncol. (2001) 19:65-70.
Tanaka et al., Nature Med. (1997) 3:437-442.
Tuschl, Chem Bioch. (2001) 2:239-245.
Uno et al., "Antisense-Mediated Suppression of Human *Heparanase* Gene Expression Inhibits Pleural Dissemination of Human Cancer Cells," Cancer Research (2001) 61:7855-7860.
Vasquez et al., Nucl. Acids Res. (1999) 27:1176-1181.
Vlodavsky et al., J. Clin. Invest (2001) 108:341-347.
Vuyisich et al., Nuc. Acids Res. (2000) 28:2369-2374.
Weinstatsaslow et al., Cancer Res. (1994) 54:6504-6511.
Wu et al., Cancer Res. (2007) 67:4123-5129.
Yoshida et al., Neurosurgery (1995) 37:287-292.
Watson et al., J. Clin. Invest. (1994) 94:261-268.
Walton et al., "Prediction of Antisense Oligonucleotide Binding Affinity to a structured RNA Target," Biotechnology and Bioengineering (1999) 65:1-9.
Weinstat-Saslow et al., "Transfection of Thrombospondin 1 Complementary DNA into a Human Breast Carcinoma Cell Line Reduces Primary Tumor Growth, Metastatic Potential, and Angiogenesis," Cancer Research (1994) 54:6504-6511.
Welch et al., Curr. Opin. Biotechnol. (1998) 9:486-496.
Welch et al., "Ribozyme Gene Therapy for Hepatitis C Virus Infection," Clinical and Diagnostic Virology (1998) 10:163-171.
Wilda et al., "Killing of Leukemic Cells with a *BCR/ABL* Fusion Gene by RNA Interference (RNAi)," Oncogene (2002) 21:5716-5724.
Wu et al., "LOXL1 and LOXL4 are Epigenetically Silenced and can Inhibit Ras/Extracellular Signal-Regulated Kinase Signaling Pathway in Human Bladder Cancer," Cancer Research (2007) 67:4123-4129.
Yoshida et al., "Copper Chelation Inhibits Tumor Angiogenesis in the Experimental 9L Gliosarcoma Model," Neurosurgery (1995) 37:287-292.
Yu et al., "RNA Interference by Expression of Short-Interfering RNAs and Hairpin RNAs in Mammalian Cells," Proceedings of the National Academy of Sciences of the United States of America (2002) 99: 6047-6052.

Office Action for EP 08 763 709.6, mailed Feb. 28, 2012, 3 pages.
Office Action for EP 08 763 709.6, mailed Apr. 20, 2011, 4 pages.
Notice of Defects in Patent Application No. 184627, mailed Jun. 18, 2012, 10 pages.
Notice of Defects in Patent Application No. 203329, mailed Jun. 18, 2012, 6 pages.
Response to office action for EP 08763709.6, filed Aug. 19, 2011, 8 pages.
European Search Report mailed Jun. 3, 2009, in EP 08020752.5-1222.
European Search Opinion mailed Jun. 3, 2009, in EP 08020752.5-1222.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
European Search Report mailed Jun. 3, 2009, in EP 08020753.3-1222.
European Search Opinion mailed Jun. 3, 2009, in EP 08020753.3-1222.
Communication pursuant to Article 94(3) EPC mailed Dec. 27, 2011, in EP 08020753.3-1222.
European Search Report mailed Jul. 13, 2011, in EP 10012458.5-2406.
European Search Opinion mailed Jul. 13, 2011, in EP 10012458.5-2406.
European Search Report mailed Jun. 27, 2011, in EP 10012457.7-2406.
European Search Opinion mailed Jun. 27, 2011, in EP 10012457.7-2406.
International Preliminary Report on Patentability Chapter I issued Jan. 19, 2010, in PCT/IL2008/000985.
Invitation to Pay Additional Fees mailed Mar. 12, 2009, (including Annex "Communication Relating to the Results of Partial International Search"), in PCT/IL2008/000985.
Written Opinion of the ISA mailed Jul. 10, 2009, in PCT/IL2008/000985.
International Search Report mailed Jul. 10, 2009, in PCT/IL2008/000985.
Communication pursuant to Article 94(3) EPC mailed Jun. 25, 2010, in EP 08763709.6-1212.
Office Action for Israeli Patent Application No. 203329, mailed Feb. 11, 2013.
Office Action for Israeli Patent Application No. 184627, mailed Feb. 12, 2013.
Decision to grant for EP 08763709.6, dated May 31, 2013.
U.S. Appl. No. 13/412,544.
Office Action dated Dec. 27, 2013, in U.S. Appl. No. 13/416,976.
Communication Pursuant to Article 94(3) EPC dated Dec. 17, 2013, in EP 12173418.0.

| | |
|---|---|
| TRCN0000046193<br>(SEQ ID 22) | CCGGCCAGATAGAGAACCTGAATATCTCGAGATATTCAGGTTCTCTATCTGGTTTTG<br>Clone ID: NM_002318.1-769s1c1<br>Accession Number(s): NM_002318.2<br>Region: CDS<br>Validation: ' Lysyl oxidase-like 2 |
| TRCN0000046194<br>(SEQ ID 23) | CCGGCCTGGGTTCAAATTTGACAATCTCGAGATTGTCAAATTTGAACCCAGGTTTTG<br>Clone ID: NM_002318.1-737s1c1<br>Accession Number(s): NM_002318.2<br>Region: CDS<br>Validation: ' Lysyl oxidase-like 2 |
| TRCN0000046195<br>(SEQ ID 24) | CCGGCGATTACTCCAACAACATCATCTCGAGATGATGTTGTTGGAGTAATCGTTTTG<br>Clone ID: NM_002318.1-2416s1c1<br>Accession Number(s): NM_002318.2<br>Region: CDS<br>Validation: ' Lysyl oxidase-like 2 |
| TRCN0000046196<br>(SEQ ID 25) | CCGGGAGGAGACATACAATACCAAACTCGAGTTTGGTATTGTATGTCTCTCTTTTG<br>Clone ID: NM_002318.1-962s1c1<br>Accession Number(s): NM_002318.2<br>Region: CDS<br>Validation: ' Lysyl oxidase-like 2 |
| TRCN0000046197<br>(SEQ ID 26) | CCGGGAAGGAGACATCCAGAAGAATCTCGAGATTCTTCTGGATGTCTCCTTCTTTTG<br>Clone ID: NM_002318.1-2237s1c1<br>Accession Number(s): NM_002318.2<br>Region: CDS<br>Validation: ' Lysyl oxidase-like 2 |

FIG. 1

|  | MCF7 Loxl2 clone 12 | MCF7 Loxl2 clone 24 | MCF7 Loxl2 WT (lentivirus infection) | MCF7 Loxl2 Y689F (lentivirus infection) |
|---|---|---|---|---|
| Acyl co-A oxidase |  |  | 5.5 |  |
| MAOA |  |  | 5.26 |  |
| Netrin 4 |  |  | 3.8 |  |
| MMP15 |  |  | 3.4 |  |
| GPCR |  |  | 2.8 |  |
| Plexin D1 |  |  | 2.7 |  |
| LDHA |  |  | 3.7 | 4.5 |
| LDHB | 24 | 26 |  |  |
| Muc1 | 8.9 | 2.3 |  |  |
| ID1 | 2.99 (5.4) | 3.39 (3) | 5.6 |  |
| HSP90α |  | 3.21 | 5.6 | 6.6 |

SEQUENCE LISTING

```
<160> NUMBER OF SEQ ID NOS: 30

<210> SEQ ID NO 1
<211> LENGTH: 2325
<212> TYPE: DNA
<213> ORGANISM: Homo sapiens

<400> SEQUENCE: 1
atggagaggc ctctgtgctc ccacctctgc agctgcctgg ctatgctggc cctcctgtcc      60
cccctgagcc tggcacagta tgacagctgg ccccattacc ccgagtactt ccagcaaccg     120
gctcctgagt atcaccagcc ccaggccccc gccaacgtgg ccaagattca gctgcgcctg     180
gctgggcaga agaggaagca cagcgagggc cgggtggagg tgtactatga tggccagtgg     240
ggcaccgtgt gcgatgacga cttctccatc cacgctgccc acgtcgtctg ccgggagctg     300
ggctatgtgg aggccaagtc ctggactgcc agctcctcct acggcaaggg agaagggccc     360
atctggttag acaatctcca ctgtactggc aacgaggcga cccttgcagc atgcacctcc     420
aatggctggg gcgtcactga ctgcaagcac acggaggatg tcggtgtggt gtgcagcgac     480
aaaaggattc ctgggttcaa atttgacaat tcgttgatca accagataga gaacctgaat     540
atccaggtgg aggacattcg gattcgagcc atcctctcaa cctaccgcaa gcgcacccca     600
gtgatggagg gctacgtgga ggtgaaggag ggcaagacct ggaagcagat ctgtgacaag     660
cactggacgg ccaagaattc ccgcgtggtc tgcggcatgt ttggcttccc tggggagagg     720
acatacaata ccaaagtgta caaatgtttt gcctcacgga ggaagcagcg ctactggcca     780
ttctccatgg actgcaccgg cacagaggcc cacatctcca gctgcaagct gggcccccag     840
gtgtcactgg accccatgaa gaatgtcacc tgcgagaatg gctaccggc cgtggtgggt     900 tgtgtgcctg gcaggtctt cagccctgac ggaccctcaa gattccggaa agcgtacaag     960
ccagagcaac cctggtgcg actgagaggc ggtgcctaca tcggggaggg ccgcgtggag    1020
```

-continued

```
gtgctcaaaa atggagaatg ggggaccgtc tgcgacgaca agtgggacct ggtgtcggcc      1080
agtgtggtct gcagagagct gggctttggg agtgccaaag aggcagtcac tggctcccga      1140
ctggggcaag ggatcggacc catccacctc aacgagatcc agtgcacagg caatgagaag      1200
tccattatag actgcaagtt caatgccgag tctcagggct gcaaccacga ggaggatgct      1260
ggtgtgagat gcaacacccc tgccatgggc ttgcagaaga agctgcgcct gaacggcggc      1320
cgcaatccct acgagggccg agtggaggtg ctggtggaga gaaacgggtc ccttgtgtgg      1380
gggatggtgt gtggccaaaa ctggggcatc gtggaggcca tggtggtctg ccgccagctg      1440
ggcctgggat cgccagcaa cgccttccag gagacctggt attggcacgg agatgtcaac      1500
agcaacaaag tggtcatgag tggagtgaag tgctcgggaa cggagctgtc cctggcgcac      1560
tgccgccacg acggggagga cgtggcctgc cccagggcg gagtgcagta cggggccgga      1620
gttgcctgct cagaaaccgc ccctgacctg gtcctcaatg cggagatggt gcagcagacc      1680
acctacctgg aggaccggcc catgttcatg ctgcagtgtg ccatggagga gaactgcctc      1740
tcggcctcag ccgcgcagac cgaccccacc acgggctacc gccggctcct gcgcttctcc      1800
tcccagatcc acaacaatgg ccagtccgac ttccggccca gaacggccg ccacgcgtgg      1860 atctggcacg actgtcacag gcactaccac agcatggagg tgttcaccca ctatgacctg      1920
ctgaacctca atggcaccaa ggtggcagag ggccacaagg ccagcttctg cttggaggac      1980
acagaatgtg aaggagacat ccagaagaat tacgagtgtg ccaacttcgg cgatcagggc      2040
atcaccatgg gctgctggga catgtaccgc atgacatcg actgccagtg ggttgacatc      2100
actgacgtgc cccctggaga ctacctgttc caggttgtta ttaaccccaa cttcgaggtt      2160
gcagaatccg attactccaa caacatcatg aaatgcagga ccgctatga cggccaccgc      2220 atctggatgt acaactgcca cataggtggt tccttcagcg aagagacgga aaaaaagttt      2280
gagcacttca gcgggctctt aaacaaccag ctgtccccgc agtaa                     2325
```

<210> SEQ ID NO 2
<211> LENGTH: 774
<212> TYPE: PRT
<213> ORGANISM: Homo sapiens

<400> SEQUENCE: 2

```
Met Glu Arg Pro Leu Cys Ser His Leu Cys Ser Cys Leu Ala Met Leu
 1               5                  10                  15

Ala Leu Leu Ser Pro Leu Ser Leu Ala Gln Tyr Asp Ser Trp Pro His
                20                  25                  30

Tyr Pro Glu Tyr Phe Gln Gln Pro Ala Pro Glu Tyr His Gln Pro Gln
            35                  40                  45

Ala Pro Ala Asn Val Ala Lys Ile Gln Leu Arg Leu Ala Gly Gln Lys
        50                  55                  60

Arg Lys His Ser Glu Gly Arg Val Glu Val Tyr Tyr Asp Gly Gln Trp
 65                  70                  75                  80

Gly Thr Val Cys Asp Asp Asp Phe Ser Ile His Ala Ala His Val Val
                85                  90                  95

Cys Arg Glu Leu Gly Tyr Val Glu Ala Lys Ser Trp Thr Ala Ser Ser
            100                 105                 110

Ser Tyr Gly Lys Gly Glu Gly Pro Ile Trp Leu Asp Asn Leu His Cys
        115                 120                 125

Thr Gly Asn Glu Ala Thr Leu Ala Ala Cys Thr Ser Asn Gly Trp Gly
    130                 135                 140
```

-continued

```
Val Thr Asp Cys Lys His Thr Glu Asp Val Gly Val Val Cys Ser Asp
145                 150                 155                 160

Lys Arg Ile Pro Gly Phe Lys Phe Asp Asn Ser Leu Ile Asn Gln Ile
                165                 170                 175

Glu Asn Leu Asn Ile Gln Val Glu Asp Ile Arg Ile Arg Ala Ile Leu
            180                 185                 190

Ser Thr Tyr Arg Lys Arg Thr Pro Val Met Glu Gly Tyr Val Glu Val
        195                 200                 205

Lys Glu Gly Lys Thr Trp Lys Gln Ile Cys Asp Lys His Trp Thr Ala
    210                 215                 220

Lys Asn Ser Arg Val Val Cys Gly Met Phe Gly Phe Pro Gly Glu Arg
225                 230                 235                 240

Thr Tyr Asn Thr Lys Val Tyr Lys Met Phe Ala Ser Arg Arg Lys Gln
                245                 250                 255

Arg Tyr Trp Pro Phe Ser Met Asp Cys Thr Gly Thr Glu Ala His Ile
                260                 265                 270

Ser Ser Cys Lys Leu Gly Pro Gln Val Ser Leu Asp Pro Met Lys Asn
        275                 280                 285

Val Thr Cys Glu Asn Gly Leu Pro Ala Val Val Gly Cys Val Pro Gly
    290                 295                 300

Gln Val Phe Ser Pro Asp Gly Pro Ser Arg Phe Arg Lys Ala Tyr Lys
305                 310                 315                 320

Pro Glu Gln Pro Leu Val Arg Leu Arg Gly Gly Ala Tyr Ile Gly Glu
                325                 330                 335

Gly Arg Val Glu Val Leu Lys Asn Gly Glu Trp Gly Thr Val Cys Asp
                340                 345                 350

Asp Lys Trp Asp Leu Val Ser Ala Ser Val Val Cys Arg Glu Leu Gly
            355                 360                 365

Phe Gly Ser Ala Lys Glu Ala Val Thr Gly Ser Arg Leu Gly Gln Gly
        370                 375                 380

Ile Gly Pro Ile His Leu Asn Glu Ile Gln Cys Thr Gly Asn Glu Lys
385                 390                 395                 400

Ser Ile Ile Asp Cys Lys Phe Asn Ala Glu Ser Gln Gly Cys Asn His
                405                 410                 415

Glu Glu Asp Ala Gly Val Arg Cys Asn Thr Pro Ala Met Gly Leu Gln
            420                 425                 430

Lys Lys Leu Arg Leu Asn Gly Gly Arg Asn Pro Tyr Glu Gly Arg Val
        435                 440                 445

Glu Val Leu Val Glu Arg Asn Gly Ser Leu Val Trp Gly Met Val Cys
    450                 455                 460

Gly Gln Asn Trp Gly Ile Val Glu Ala Met Val Val Cys Arg Gln Leu
465                 470                 475                 480

Gly Leu Gly Phe Ala Ser Asn Ala Phe Gln Glu Thr Trp Tyr Trp His
                485                 490                 495

Gly Asp Val Asn Ser Asn Lys Val Val Met Ser Gly Val Lys Cys Ser
            500                 505                 510

Gly Thr Glu Leu Ser Leu Ala His Cys Arg His Asp Gly Glu Asp Val
        515                 520                 525

Ala Cys Pro Gln Gly Gly Val Gln Tyr Gly Ala Gly Val Ala Cys Ser
    530                 535                 540

Glu Thr Ala Pro Asp Leu Val Leu Asn Ala Glu Met Val Gln Gln Thr
545                 550                 555                 560
```

```
Thr Tyr Leu Glu Asp Arg Pro Met Phe Met Leu Gln Cys Ala Met Glu
            565                 570                 575

Glu Asn Cys Leu Ser Ala Ser Ala Ala Gln Thr Asp Pro Thr Thr Gly
        580                 585                 590

Tyr Arg Arg Leu Leu Arg Phe Ser Ser Gln Ile His Asn Asn Gly Gln
        595                 600                 605

Ser Asp Phe Arg Pro Lys Asn Gly Arg His Ala Trp Ile Trp His Asp
    610                 615                 620

Cys His Arg His Tyr His Ser Met Glu Val Phe Thr His Tyr Asp Leu
625                 630                 635                 640

Leu Asn Leu Asn Gly Thr Lys Val Ala Glu Gly His Lys Ala Ser Phe
                645                 650                 655

Cys Leu Glu Asp Thr Glu Cys Glu Gly Asp Ile Gln Lys Asn Tyr Glu
            660                 665                 670

Cys Ala Asn Phe Gly Asp Gln Gly Ile Thr Met Gly Cys Trp Asp Met
        675                 680                 685

Tyr Arg His Asp Ile Asp Cys Gln Trp Val Asp Ile Thr Asp Val Pro
        690                 695                 700

Pro Gly Asp Tyr Leu Phe Gln Val Val Ile Asn Pro Asn Phe Glu Val
705                 710                 715                 720

Ala Glu Ser Asp Tyr Ser Asn Asn Ile Met Lys Cys Arg Ser Arg Tyr
                725                 730                 735

Asp Gly His Arg Ile Trp Met Tyr Asn Cys His Ile Gly Gly Ser Phe
            740                 745                 750

Ser Glu Glu Thr Glu Lys Lys Phe Glu His Phe Ser Gly Leu Leu Asn
        755                 760                 765

Asn Gln Leu Ser Pro Gln
        770

<210> SEQ ID NO 3
<211> LENGTH: 757
<212> TYPE: PRT
<213> ORGANISM: Homo sapiens

<400> SEQUENCE: 3

Met Met Trp Pro Gln Pro Pro Thr Phe Ser Leu Phe Leu Leu Leu Leu
1               5                   10                  15

Leu Ser Gln Ala Pro Ser Ser Arg Pro Gln Ser Ser Gly Thr Lys Lys
            20                  25                  30

Leu Arg Leu Val Gly Pro Ala Asp Arg Pro Glu Glu Gly Arg Leu Glu
        35                  40                  45

Val Leu His Gln Gly Gln Trp Gly Thr Val Cys Asp Asp Asp Phe Ala
50                  55                  60

Leu Gln Glu Ala Thr Val Ala Cys Arg Gln Leu Gly Phe Glu Ser Ala
65                  70                  75                  80

Leu Thr Trp Ala His Ser Ala Lys Tyr Gly Gln Gly Glu Gly Pro Ile
                85                  90                  95

Trp Leu Asp Asn Val Arg Cys Leu Gly Thr Glu Lys Thr Leu Asp Gln
            100                 105                 110

Cys Gly Ser Asn Gly Trp Gly Ile Ser Asp Cys Arg His Ser Glu Asp
        115                 120                 125

Val Gly Val Val Cys His Pro Arg Arg Gln His Gly Tyr His Ser Glu
    130                 135                 140

Lys Val Ser Asn Ala Leu Gly Pro Gln Gly Arg Arg Leu Glu Glu Val
145                 150                 155                 160
```

-continued

Arg Leu Lys Pro Ile Leu Ala Ser Ala Lys Arg His Ser Pro Val Thr
                165                 170                 175

Glu Gly Ala Val Glu Val Arg Tyr Asp Gly His Trp Arg Gln Val Cys
            180                 185                 190

Asp Gln Gly Trp Thr Met Asn Asn Ser Arg Val Val Cys Gly Met Leu
        195                 200                 205

Gly Phe Pro Ser Gln Thr Ser Val Asn Ser His Tyr Tyr Arg Lys Val
    210                 215                 220

Trp Asn Leu Lys Met Lys Asp Pro Lys Ser Arg Leu Asn Ser Leu Thr
225                 230                 235                 240

Lys Lys Asn Ser Phe Trp Ile His Arg Val Asp Cys Phe Gly Thr Glu
                245                 250                 255

Pro His Leu Ala Lys Cys Gln Val Gln Val Ala Pro Gly Arg Gly Lys
            260                 265                 270

Leu Arg Pro Ala Cys Pro Gly Met His Ala Val Ser Cys Val
        275                 280                 285

Ala Gly Pro His Phe Arg Arg Gln Lys Pro Lys Pro Thr Arg Lys Glu
    290                 295                 300

Ser His Ala Glu Glu Leu Lys Val Arg Leu Arg Ser Gly Ala Gln Val
305                 310                 315                 320

Gly Glu Gly Arg Val Glu Val Leu Met Asn Arg Gln Trp Gly Thr Val
                325                 330                 335

Cys Asp His Arg Trp Asn Leu Ile Ser Ala Ser Val Val Cys Arg Gln
            340                 345                 350

Leu Gly Phe Gly Ser Ala Arg Glu Ala Leu Phe Gly Ala Gln Leu Gly
        355                 360                 365

Gln Gly Leu Gly Pro Ile His Leu Ser Glu Val Arg Cys Arg Gly Tyr
    370                 375                 380

Glu Arg Thr Leu Gly Asp Cys Leu Ala Leu Glu Gly Ser Gln Asn Gly
385                 390                 395                 400

Cys Gln His Ala Asn Asp Ala Ala Val Arg Cys Asn Ile Pro Asp Met
                405                 410                 415

Gly Phe Gln Asn Lys Val Arg Leu Ala Gly Gly Arg Asn Ser Glu Glu
            420                 425                 430

Gly Val Val Glu Val Gln Val Glu Val Asn Gly Gly Pro Arg Trp Gly
        435                 440                 445

Thr Val Cys Ser Asp His Trp Gly Leu Thr Glu Ala Met Val Thr Cys
    450                 455                 460

Arg Gln Leu Gly Leu Gly Phe Ala Asn Phe Ala Leu Lys Asp Thr Trp
465                 470                 475                 480

Tyr Trp Gln Gly Thr Pro Glu Ala Lys Glu Val Val Met Ser Gly Val
                485                 490                 495

Arg Cys Ser Gly Thr Glu Met Ala Leu Gln Gln Cys Gln Arg His Gly
            500                 505                 510

Pro Val His Cys Ser His Gly Pro Gly Arg Phe Ser Ala Gly Val Ala
        515                 520                 525

Cys Met Asn Ser Ala Pro Asp Leu Val Met Asn Ala Gln Leu Val Gln
    530                 535                 540

Glu Thr Ala Tyr Leu Glu Asp Arg Pro Leu Ser Met Leu Tyr Cys Ala
545                 550                 555                 560

His Glu Glu Asn Cys Leu Ser Lys Ser Ala Asp His Met Asp Trp Pro
                565                 570                 575

```
Tyr Gly Tyr Arg Arg Leu Leu Arg Phe Ser Ser Gln Ile Tyr Asn Leu
            580                 585                 590

Gly Arg Ala Asp Phe Arg Pro Lys Ala Gly Arg His Ser Trp Ile Trp
        595                 600                 605

His Gln Cys His Arg His Asn His Ser Ile Glu Val Phe Thr His Tyr
    610                 615                 620

Asp Leu Leu Thr Leu Asn Gly Ser Lys Val Ala Glu Gly His Lys Ala
625                 630                 635                 640

Ser Phe Cys Leu Glu Asp Thr Asn Cys Pro Ser Gly Val Gln Arg Arg
                645                 650                 655

Tyr Ala Cys Ala Asn Phe Gly Glu Gln Gly Val Ala Val Gly Cys Trp
            660                 665                 670

Asp Thr Tyr Arg His Asp Ile Asp Cys Gln Trp Val Asp Ile Thr Asp
        675                 680                 685

Val Gly Pro Gly Asp Tyr Ile Phe Gln Val Val Asn Pro Thr Asn
    690                 695                 700

Asp Val Ala Glu Ser Asp Phe Ser Asn Asn Met Ile Arg Cys Arg Cys
705                 710                 715                 720

Lys Tyr Asp Gly Gln Arg Val Trp Leu His Asn Cys His Thr Gly Asp
                725                 730                 735

Ser Tyr Arg Ala Asn Ala Glu Leu Ser Leu Glu Gln Glu Gln Arg Leu
            740                 745                 750

Arg Asn Asn Leu Ile
        755

<210> SEQ ID NO 4
<211> LENGTH: 2262
<212> TYPE: DNA
<213> ORGANISM: Homo sapiens

<400> SEQUENCE: 4
```

| | | | | | |
|---|---|---|---|---|---|
| atgcgacctg | tcagtgtctg | gcagtggagc | ccctgggggc | tgctgctgtg | cctgctgtgc | 60 |
| agttcgtgct | gggggtctcc | gtcccccttcc | acgggccctg | agaagaaggc | cgggagccag | 120 |
| ggcttcggt | tccggctggc | tggcttcccc | aggaagccct | acgagggccg | cgtggagata | 180 |
| cagcgagctg | gtgaatgggg | caccatctgc | gatgatgact | tcacgctgca | ggctgcccac | 240 |
| atcctctgcc | gggagctggg | cttcacagag | gccacaggct | ggaccccacag | tgccaaatat | 300 |
| ggccctggaa | caggccgcat | ctggctggac | aacttgagct | gcagtgggac | cgagcagagt | 360 |
| gtgactgaat | gtgcctcccg | gggctggggg | aacagtgact | gtacgcacga | tgaggatgct | 420 |
| ggggtcatct | gcaaagacca | gcgcctccct | ggcttctcgg | actccaatgt | cattgaggta | 480 |
| gagcatcacc | tgcaagtgga | ggaggtgcga | attcgacccg | ccgttgggtg | gggcagacga | 540 |
| ccccctgcccg | tgacggaggg | gctggtggaa | gtcaggcttc | ctgacggctg | gtcgcaagtg | 600 |
| tgcgacaaag | gctggagcgc | ccacaacagc | acgtggtctc | gcgggatgct | gggcttcccc | 660 |
| agcgaaaaga | gggtcaacgc | ggccttctac | aggctgctag | cccaacggca | gcaacactcc | 720 |
| tttggtctgc | atgggtggc | gtgcgtgggc | acggaggccc | acctctccct | ctgttccctg | 780 |
| gagttctatc | gtgccaatga | caccgccagg | tgccctgggg | gggccctgc | agtggtgagc | 840 |
| tgtgtgccag | gccctgtcta | gcggcatcc | agtggccaga | agaagcaaca | acagtcgaag | 900 |
| cctcaggggg | aggccgtgt | ccgtctaaag | gcggcgcccc | acctggaga | gggccgggta | 960 |
| gaagtcctga | aggccagcac | atggggcaca | gtctgtgacc | gcaagtggga | cctgcatgca | 1020 |
| gccagcgtgg | tgtgtcggga | gctgggcttc | gggagtgctc | gagaagctct | gagtggcgct | 1080 |

```
cgcatggggc agggcatggg tgctatccac ctgagtgaag ttcgctgctc tggacaggag   1140
ctctccctct ggaagtgccc ccacaagaac atcacagctg aggattgttc acatagccag   1200
gatgccgggg tccggtgcaa cctaccttac actggggcag agaccaggat ccgactcagt   1260
gggggccgca gccaacatga ggggcgagtc gaggtgcaaa taggggggacc tgggcccctt   1320 cgctggggcc tcatctgtgg ggatgactgg gggaccctgg aggccatggt ggcctgtagg   1380
caactgggtc tgggctacgc caaccacggc ctgcaggaga cctggtactg ggactctggg   1440
aatataacag aggtggtgat gagtggagtg cgctgcacag ggactgagct gtccctggat   1500
cagtgtgccc atcatggcac ccacatcacc tgcaagagga cagggacccg cttcactgct   1560
ggagtcatct gttctgagac tgcatcagat ctgttgctgc actcagcact ggtgcaggag   1620
accgcctaca tcgaagaccg gcccctgcat atgttgtact gtgctgcgga agagaactgc   1680
ctggccagct cagcccgctc agccaactgg ccctatggtc accggcgtct gctccgattc   1740
tcctcccaga tccacaacct gggacgagct gacttcaggc caaggctgg gcgccactcc    1800 tgggtgtggc acgagtgcca tgggcattac acagcatgg acatcttcac tcactatgat    1860
atcctcaccc caaatggcac caaggtggct gagggccaca aagctagttt ctgtctcgaa   1920
gacactgagt gtcaggagga tgtctccaag cggtatgagt gtgccaactt ggagagcaa    1980 ggcatcactg tgggttgctg ggatctctac cggcatgaca ttgactgtca gtggattgac   2040
atcacggatg tgaagccagg aaactacatt ctccaggttg tcatcaaccc aaactttgaa   2100
gtagcagaga gtgactttac caacaatgca atgaaatgta actgcaaata tgatggacat   2160
agaatctggg tgcacaactg ccacattggt gatgccttca gtgaagaggc caacaggagg   2220
tttgaacgct accctggcca gaccagcaac cagattatct aa                      2262

<210> SEQ ID NO 5
<211> LENGTH: 1725
<212> TYPE: DNA
<213> ORGANISM: Homo sapiens

<400> SEQUENCE: 5
atggctctgg cccgaggcag ccggcagctg ggggccctgg tgtggggcgc ctgcctgtgc     60
gtgctggtgc acgggcagca ggcgcagccc gggcagggct cggacccgc ccgctggcgg    120 cagctgatcc agtgggagaa caacgggcag gtgtacagct tgctcaactc gggctcagag   180
tacgtgccgg ccggacctca gcgctccgag agtagctccc gggtgctgct ggccggcgcg   240
ccccaggccc agcagcggcg cagccacggg agccccggc gtcggcaggc gccgtccctg    300
cccctgccgg ggcgcgtggg ctcggacacc gtgcgcggcc aggcgcggca cccattcggc   360
tttggccagt gcccgacaa ctggcgcgag gtggccgtcg gggacagcac gggcatggcc    420
ctggcccgca cctccgtctc ccagcaacgg cacgggggct ccgcctcctc ggtctcggct   480
tcggccttcg ccagcaccta ccgccagcag ccctcctacc gcagcagtt cccctacccg    540 caggcgccct tcgtcagcca gtacgagaac tacgaccccg cgtcgcggac ctacgaccag    600
ggtttcgtgt actaccggcc cgcgggcggc ggcgtgggcg cggggggcgg ggccgtggcc   660
tcggcggggg tcatctaccc ctaccagccc cgggcgcgct acgaggagta cggcggcggc   720
gaagagctgc ccgagtaccc gcctcagggc ttctaccgg ccccgagag ccctacgtg    780 ccgccgccgc cgccgccccc cgacggcctg accgccgct actcgcacag tctgtacagc   840
gagggcaccc ccggcttcga gcaggcctac cctgaccccg tcccgaggc ggcgcaggcc   900
```

```
catggcggag acccacgcct gggctggtac ccgccctacg ccaacccgcc gcccgaggcg    960
tacgggccgc cgcgcgcgct ggagccgccc tacctgccgg tgcgcagctc cgacacgccc   1020
ccgccgggtg gggagcggaa cggcgcgcag cagggccgcc tcagcgtagg cagcgtgtac   1080
cggcccaacc agaacggccg cggtctccct gacttggtcc cagacccaa ctatgtgcaa    1140
gcatccactt atgtgcagag agcccacctg tactccctgc gctgtgctgc ggaggagaag   1200
tgtctggcca gcacagccta tgcccctgag gccaccgact acgatgtgcg ggtgctactg   1260
cgcttccccc agcgcgtgaa gaaccagggc acagcagact tcctcccaa ccggccacgg    1320
cacacctggg agtggcacag ctgccaccag cattaccaca gcatggacga gttcagccac   1380
tacgacctac tggatgcagc cacaggcaag aaggtggccg agggccacaa ggccagtttc   1440
tgcctggagg acagcacctg tgacttcggc aacctcaagc gctatgcatg cacctctcat   1500
acccagggcc tgagcccagg ctgctatgac acctacaatg cggacatcga ctgccagtgg   1560
atcgacataa ccgacgtgca gcctgggaac tacatcctca aggtgcacgt gaacccaaag   1620
tatattgttt tggagtctga cttcaccaac aacgtggtga gatgcaacat tcactacaca   1680
ggtcgctacg tttctgcaac aaactgcaaa attgtccaat cctga                  1725
```

<210> SEQ ID NO 6
<211> LENGTH: 574
<212> TYPE: PRT
<213> ORGANISM: Homo sapiens

<400> SEQUENCE: 6

```
Met Ala Leu Ala Arg Gly Ser Arg Gln Leu Gly Ala Leu Val Trp Gly
  1               5                  10                  15

Ala Cys Leu Cys Val Leu Val His Gly Gln Gln Ala Gln Pro Gly Gln
             20                  25                  30

Gly Ser Asp Pro Ala Arg Trp Arg Gln Leu Ile Gln Trp Glu Asn Asn
         35                  40                  45

Gly Gln Val Tyr Ser Leu Leu Asn Ser Gly Ser Glu Tyr Val Pro Ala
     50                  55                  60

Gly Pro Gln Arg Ser Glu Ser Ser Ser Arg Val Leu Leu Ala Gly Ala
 65                  70                  75                  80

Pro Gln Ala Gln Gln Arg Arg Ser His Gly Ser Pro Arg Arg Gln
                 85                  90                  95

Ala Pro Ser Leu Pro Leu Pro Gly Arg Val Gly Ser Asp Thr Val Arg
            100                 105                 110

Gly Gln Ala Arg His Pro Phe Gly Phe Gly Gln Val Pro Asp Asn Trp
        115                 120                 125

Arg Glu Val Ala Val Gly Asp Ser Thr Gly Met Ala Leu Ala Arg Thr
    130                 135                 140

Ser Val Ser Gln Gln Arg His Gly Gly Ser Ala Ser Ser Val Ser Ala
145                 150                 155                 160

Ser Ala Phe Ala Ser Thr Tyr Arg Gln Gln Pro Ser Tyr Pro Gln Gln
                165                 170                 175

Phe Pro Tyr Pro Gln Ala Pro Phe Val Ser Gln Tyr Glu Asn Tyr Asp
            180                 185                 190

Pro Ala Ser Arg Thr Tyr Asp Gln Gly Phe Val Tyr Arg Pro Ala
        195                 200                 205

Gly Gly Gly Val Gly Ala Gly Ala Ala Val Ala Ser Ala Gly Val
    210                 215                 220

Ile Tyr Pro Tyr Gln Pro Arg Ala Arg Tyr Glu Glu Tyr Gly Gly Gly
```

```
                225                 230                 235                 240
Glu Glu Leu Pro Glu Tyr Pro Gln Gly Phe Tyr Pro Ala Pro Glu
                    245                 250                 255
Arg Pro Tyr Val Pro Pro Pro Pro Pro Asp Gly Leu Asp Arg
                260                 265                 270
Arg Tyr Ser His Ser Leu Tyr Ser Glu Gly Thr Pro Gly Phe Glu Gln
                275                 280                 285
Ala Tyr Pro Asp Pro Gly Pro Glu Ala Ala Gln Ala His Gly Gly Asp
            290                 295                 300
Pro Arg Leu Gly Trp Tyr Pro Tyr Ala Asn Pro Pro Glu Ala
305                 310                 315                 320
Tyr Gly Pro Pro Arg Ala Leu Glu Pro Pro Tyr Leu Pro Val Arg Ser
                        325                 330                 335
Ser Asp Thr Pro Pro Gly Gly Glu Arg Asn Gly Ala Gln Gln Gly
                    340                 345                 350
Arg Leu Ser Val Gly Ser Val Tyr Arg Pro Asn Gln Asn Gly Arg Gly
                355                 360                 365
Leu Pro Asp Leu Val Pro Asp Pro Asn Tyr Val Gln Ala Ser Thr Tyr
        370                 375                 380
Val Gln Arg Ala His Leu Tyr Ser Leu Arg Cys Ala Ala Glu Glu Lys
385                 390                 395                 400
Cys Leu Ala Ser Thr Ala Tyr Ala Pro Glu Ala Thr Asp Tyr Asp Val
                        405                 410                 415
Arg Val Leu Leu Arg Phe Pro Gln Arg Val Lys Asn Gln Gly Thr Ala
                420                 425                 430
Asp Phe Leu Pro Asn Arg Pro Arg His Thr Trp Glu Trp His Ser Cys
            435                 440                 445
His Gln His Tyr His Ser Met Asp Glu Phe Ser His Tyr Asp Leu Leu
        450                 455                 460
Asp Ala Ala Thr Gly Lys Lys Val Ala Glu Gly His Lys Ala Ser Phe
465                 470                 475                 480
Cys Leu Glu Asp Ser Thr Cys Asp Phe Gly Asn Leu Lys Arg Tyr Ala
                    485                 490                 495
Cys Thr Ser His Thr Gln Gly Leu Ser Pro Gly Cys Tyr Asp Thr Tyr
                500                 505                 510
Asn Ala Asp Ile Asp Cys Gln Trp Ile Asp Ile Thr Asp Val Gln Pro
            515                 520                 525
Gly Asn Tyr Ile Leu Lys Val His Val Asn Pro Lys Tyr Ile Val Leu
        530                 535                 540
Glu Ser Asp Phe Thr Asn Asn Val Val Arg Cys Asn Ile His Tyr Thr
545                 550                 555                 560
Gly Arg Tyr Val Ser Ala Thr Asn Cys Lys Ile Val Gln Ser
                    565                 570

<210> SEQ ID NO 7
<211> LENGTH: 1254
<212> TYPE: DNA
<213> ORGANISM: Homo sapiens

<400> SEQUENCE: 7
atgcgcttcg cctggaccgt gctcctgctc gggcctttgc agctctgcgc gctagtgcac      60
tgcgcccctc ccgccgccgg ccaacagcag ccccgcgcg agccgccggc ggctccgggc      120
gcctggcgcc agcagatcca atgggagaac aacgggcagg tgttcagctt gctgagcctg      180
```

```
ggctcacagt accagcctca gcgccgccgg gacccgggcg ccgccgtccc tggtgcagcc    240
aacgcctccg cccagcagcc ccgcactccg atcctgctga tccgcgacaa ccgcaccgcc    300
gcggcgcgaa cgcggacggc cggctcatct ggagtcaccg ctggccgccc caggcccacc    360
gcccgtcact ggttccaagc tggctactcg acatctagag cccgcgaagc tggcgcctcg    420
cgcgcggaga accagacagc gccgggagaa gttcctgcgc tcagtaacct gcggccgccc    480
agccgcgtgg acggcatggt gggcgacgac ccttacaacc cctacaagta ctctgacgac    540
aacccttatt acaactacta cgatacttat gaaaggccca gacctggggg caggtaccgg    600
cccggatacg gcactggcta cttccagtac ggtctcccag acctggtggc cgacccctac    660
tacatccagg cgtccacgta cgtgcagaag atgtccatgt acaacctgag atgcgcggcg    720
gaggaaaact gtctggccag tacagcatac agggcagatg tcagagatta tgatcacagg    780
gtgctgctca gatttcccca agagtgaaaa accaaggga catcagattt cttacccagc    840
cgaccaagat attcctggga atggcacagt tgtcatcaac attaccacag tatggatgag    900
tttagccact atgacctgct tgatgccaac acccagagga gagtggctga aggccacaaa    960
gcaagtttct gtcttgaaga cacatcctgt gactatggct accacaggcg atttgcatgt   1020
actgcacaca cacagggatt gagtcctggc tgttatgata cctatggtgc agacatagac   1080
tgccagtgga ttgatattac agatgtaaaa cctggaaact atatcctaaa ggtcagtgta   1140
aaccccagct acctggttcc tgaatctgac ataccaaca atgttgtgcg ctgtgacatt    1200
cgctacacag gacatcatgc gtatgcctca ggctgcacaa tttcaccgta ttag          1254
```

<210> SEQ ID NO 8
<211> LENGTH: 417
<212> TYPE: PRT
<213> ORGANISM: Homo sapiens

<400> SEQUENCE: 8

Met Arg Phe Ala Trp Thr Val Leu Leu Gly Pro Leu Gln Leu Cys
  1               5                  10                  15

Ala Leu Val His Cys Ala Pro Pro Ala Gly Gln Gln Gln Pro Pro
                 20                  25                  30

Arg Glu Pro Pro Ala Ala Pro Gly Ala Trp Arg Gln Gln Ile Gln Trp
                 35                  40                  45

Glu Asn Asn Gly Gln Val Phe Ser Leu Ser Leu Gly Ser Gln Tyr
 50                  55                  60

Gln Pro Gln Arg Arg Asp Pro Gly Ala Val Pro Gly Ala Ala
 65                  70                  75                  80

Asn Ala Ser Ala Gln Gln Pro Arg Thr Pro Ile Leu Leu Ile Arg Asp
                 85                  90                  95

Asn Arg Thr Ala Ala Ala Arg Thr Arg Thr Ala Gly Ser Ser Gly Val
                100                 105                 110

Thr Ala Gly Arg Pro Arg Pro Thr Ala Arg His Trp Phe Gln Ala Gly
                115                 120                 125

Tyr Ser Thr Ser Arg Ala Arg Glu Ala Gly Ala Ser Arg Ala Glu Asn
                130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Asp Pro Tyr Asn Pro Tyr Lys
                165                 170                 175

Tyr Ser Asp Asp Asn Pro Tyr Tyr Asn Tyr Tyr Asp Thr Tyr Glu Arg
                180                 185                 190

```
Pro Arg Pro Gly Gly Arg Tyr Arg Pro Gly Tyr Gly Thr Gly Tyr Phe
        195                 200                 205
Gln Tyr Gly Leu Pro Asp Leu Val Ala Asp Pro Tyr Tyr Ile Gln Ala
    210                 215                 220
Ser Thr Tyr Val Gln Lys Met Ser Met Tyr Asn Leu Arg Cys Ala Ala
225                 230                 235                 240
Glu Glu Asn Cys Leu Ala Ser Thr Ala Tyr Arg Ala Asp Val Arg Asp
                245                 250                 255
Tyr Asp His Arg Val Leu Leu Arg Phe Pro Gln Arg Val Lys Asn Gln
            260                 265                 270
Gly Thr Ser Asp Phe Leu Pro Ser Arg Pro Arg Tyr Ser Trp Glu Trp
        275                 280                 285
His Ser Cys His Gln His Tyr His Ser Met Asp Glu Phe Ser His Tyr
    290                 295                 300
Asp Leu Leu Asp Ala Asn Thr Gln Arg Arg Val Ala Glu Gly His Lys
305                 310                 315                 320
Ala Ser Phe Cys Leu Glu Asp Thr Ser Cys Asp Tyr Gly Tyr His Arg
                325                 330                 335
Arg Phe Ala Cys Thr Ala His Thr Gln Gly Leu Ser Pro Gly Cys Tyr
            340                 345                 350
Asp Thr Tyr Gly Ala Asp Ile Asp Cys Gln Trp Ile Asp Ile Thr Asp
        355                 360                 365
Val Lys Pro Gly Asn Tyr Ile Leu Lys Val Ser Val Asn Pro Ser Tyr
    370                 375                 380
Leu Val Pro Glu Ser Asp Tyr Thr Asn Asn Val Val Arg Cys Asp Ile
385                 390                 395                 400
Arg Tyr Thr Gly His His Ala Tyr Ala Ser Gly Cys Thr Ile Ser Pro
                405                 410                 415
Tyr

<210> SEQ ID NO 9
<211> LENGTH: 752
<212> TYPE: PRT
<213> ORGANISM: Homo sapiens

<400> SEQUENCE: 9

Met Arg Pro Val Ser Val Trp Gln Trp Ser Pro Trp Gly Leu Leu Leu
1               5                   10                  15
Cys Leu Leu Cys Ser Ser Cys Leu Gly Ser Pro Ser Pro Ser Thr Gly
                20                  25                  30
Pro Glu Lys Lys Ala Gly Ser Gln Gly Leu Arg Phe Arg Leu Ala Gly
            35                  40                  45
Phe Pro Arg Lys Pro Tyr Glu Gly Arg Val Glu Ile Gln Arg Ala Gly
        50                  55                  60
Glu Trp Gly Thr Ile Cys Asp Asp Asp Phe Thr Leu Gln Ala Ala His
65                  70                  75                  80
Ile Leu Cys Arg Glu Leu Gly Phe Thr Glu Ala Thr Gly Trp Thr His
                85                  90                  95
Ser Ala Lys Tyr Gly Pro Gly Thr Gly Arg Ile Trp Leu Asp Asn Leu
            100                 105                 110
Ser Cys Ser Gly Thr Glu Gln Ser Val Thr Glu Cys Ala Ser Arg Gly
        115                 120                 125
Trp Gly Asn Ser Asp Cys Thr His Asp Glu Asp Ala Gly Val Ile Cys
    130                 135                 140
```

```
Lys Asp Gln Arg Leu Pro Gly Phe Ser Asp Ser Asn Val Ile Glu Val
145                 150                 155                 160

Glu His His Leu Gln Val Glu Val Arg Ile Arg Pro Ala Val Gly
                165                 170                 175

Trp Gly Arg Arg Pro Leu Pro Val Thr Glu Gly Leu Val Glu Val Arg
            180                 185                 190

Leu Pro Asp Gly Trp Ser Gln Val Cys Asp Lys Gly Trp Ser Ala His
            195                 200                 205

Asn Ser His Val Val Cys Gly Met Leu Gly Phe Pro Ser Glu Lys Arg
            210                 215                 220

Val Asn Ala Ala Phe Tyr Arg Leu Leu Ala Gln Arg Gln His Ser
225                 230                 235                 240

Phe Gly Leu His Gly Val Ala Cys Val Gly Thr Glu Ala His Leu Ser
                245                 250                 255

Leu Cys Ser Leu Glu Phe Tyr Arg Ala Asn Asp Thr Ala Arg Cys Pro
                260                 265                 270

Gly Gly Gly Pro Ala Val Val Ser Cys Val Pro Gly Pro Val Tyr Ala
            275                 280                 285

Ala Ser Ser Gly Gln Lys Gln Gln Gln Ser Lys Pro Gln Gly Glu
290                 295                 300

Ala Arg Val Arg Leu Lys Gly Ala His Pro Gly Glu Gly Arg Val
305                 310                 315                 320

Glu Val Leu Lys Ala Ser Thr Trp Gly Thr Val Cys Asp Arg Lys Trp
                325                 330                 335

Asp Leu His Ala Ala Ser Val Val Cys Arg Glu Leu Gly Phe Gly Ser
            340                 345                 350

Ala Arg Glu Ala Leu Ser Gly Ala Arg Met Gly Gln Gly Met Gly Ala
                355                 360                 365

Ile His Leu Ser Glu Val Arg Cys Ser Gly Gln Glu Leu Ser Leu Trp
            370                 375                 380

Lys Cys Pro His Lys Asn Ile Thr Ala Glu Asp Cys Ser His Ser Gln
385                 390                 395                 400

Asp Ala Gly Val Arg Cys Asn Leu Pro Tyr Thr Gly Ala Glu Thr Arg
                405                 410                 415

Ile Arg Leu Ser Gly Gly Arg Ser Gln His Glu Gly Arg Val Glu Val
                420                 425                 430

Gln Ile Gly Gly Pro Gly Pro Leu Arg Trp Gly Leu Ile Cys Gly Asp
            435                 440                 445

Asp Trp Gly Thr Leu Glu Ala Met Val Ala Cys Arg Gln Leu Gly Leu
            450                 455                 460

Gly Tyr Ala Asn His Gly Leu Gln Glu Thr Trp Tyr Trp Asp Ser Gly
465                 470                 475                 480

Asn Ile Thr Glu Val Val Met Ser Gly Val Arg Cys Thr Gly Thr Glu
                485                 490                 495

Leu Ser Leu Asp Gln Cys Ala His His Gly Thr His Ile Thr Cys Lys
                500                 505                 510

Arg Thr Gly Thr Arg Phe Thr Ala Gly Val Ile Cys Ser Glu Thr Ala
                515                 520                 525

Ser Asp Leu Leu Leu His Ser Ala Leu Val Gln Glu Thr Ala Tyr Ile
                530                 535                 540

Glu Asp Arg Pro Leu His Met Leu Tyr Cys Ala Ala Glu Glu Asn Cys
545                 550                 555                 560
```

Leu Ala Ser Ser Ala Arg Ser Ala Asn Trp Pro Tyr Gly His Arg Arg
            565                 570                 575

Leu Leu Arg Phe Ser Ser Gln Ile His Asn Leu Gly Arg Ala Asp Phe
        580                 585                 590

Arg Pro Lys Ala Gly Arg His Ser Trp Val Trp His Glu Cys His Gly
    595                 600                 605

His Tyr His Ser Met Asp Ile Phe Thr His Tyr Asp Ile Leu Thr Pro
610                 615                 620

Asn Gly Thr Lys Val Ala Glu Gly His Lys Ala Ser Phe Cys Leu Glu
625                 630                 635                 640

Asp Thr Glu Cys Gln Glu Asp Val Ser Lys Arg Tyr Glu Cys Ala Asn
            645                 650                 655

Phe Gly Glu Gln Gly Ile Thr Val Gly Cys Trp Asp Leu Tyr Arg His
        660                 665                 670

Asp Ile Asp Cys Gln Trp Ile Asp Ile Thr Asp Val Lys Pro Gly Asn
    675                 680                 685

Tyr Ile Leu Gln Val Val Ile Asn Pro Asn Phe Glu Val Ala Glu Ser
690                 695                 700

Asp Phe Thr Asn Asn Ala Met Lys Cys Asn Cys Lys Tyr Asp Gly His
705                 710                 715                 720

Arg Ile Trp Val His Asn Cys His Ile Gly Asp Ala Phe Ser Glu Glu
            725                 730                 735

Ala Asn Arg Arg Phe Glu Arg Tyr Pro Gly Gln Thr Ser Asn Gln Ile
        740                 745                 750

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 10
cgcaagcttg gatccgggat ggagaggcct ctgtgc                          36

<210> SEQ ID NO 11
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 11
cgctctagag gatccttact gcggggacag ctggttg                         37

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
gccatgcgac ctgtcagtgt c                                          21

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
gggcagtggc acttagat                                                        18

<210> SEQ ID NO 14
<211> LENGTH: 613
<212> TYPE: DNA
<213> ORGANISM: Homo sapiens

<400> SEQUENCE: 14
ccctgacctg gtcctcaatg cggagatggt gcagcagacc acctacctgg aggaccggcc         60
catgttcatg ctgcagtgtg ccatggagga gaactgcctc tcggcctcag ccgcgcagac        120
cgaccccacc acgggctacc gccggctcct gcgcttctcc tcccagatcc acaacaatgg        180
ccagtccgac ttccggccca gaacggccg ccacgcgtgg atctggcacg actgtcacag         240
gcactaccac agcatggagg tgttcaccca ctatgacctg ctgaacctca atggcaccaa        300
ggtggcagag ggccacaagg ccagcttctg cttggaggac acagaatgtg aaggagacat        360
ccagaagaat tacgagtgtg ccaacttcgg cgatcagggc atcaccatgg gctgctggga        420
catgtaccgc catgacatcg actgccagtg ggttgacatc actgacgtgc cccctggaga        480
ctacctgttc caggttgtta ttaaccccca cttcgaggtt gcagaatccg attactccaa        540
caacatcatg aaatgcagga gccgctatga cggccaccgc atctggatgt acaactgcca        600
cataggtggt tcc                                                           613

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
acatgcatgc cctgacctgg tcctcaatgc                                          30

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
cccaagcttg gaaccaccta tgtggcagtt                                          30

<210> SEQ ID NO 17
<211> LENGTH: 210
<212> TYPE: PRT
<213> ORGANISM: Artificial Sequence
<220> FEATURE:
<223> OTHER INFORMATION: Protein sequence derived from fusion of LOXL2
      fragment (1641-2253) to a 5' 6XHis tag

<400> SEQUENCE: 17

His His His His His His Pro Asp Leu Val Leu Asn Ala Glu Met Val
 1               5                  10                  15

Gln Gln Thr Thr Tyr Leu Glu Asp Arg Pro Met Phe Met Leu Gln Cys
            20                  25                  30

Ala Met Glu Glu Asn Cys Leu Ser Ala Ser Ala Ala Gln Thr Asp Pro
        35                  40                  45

```
Thr Thr Gly Tyr Arg Arg Leu Leu Arg Phe Ser Ser Gln Ile His Asn
    50                  55                  60

Asn Gly Gln Ser Asp Phe Arg Pro Lys Asn Gly Arg His Ala Trp Ile
 65                  70                  75                  80

Trp His Asp Cys His Arg His Tyr Ser Met Glu Val Phe Thr His
                 85                  90                  95

Tyr Asp Leu Leu Asn Leu Asn Gly Thr Lys Val Ala Glu Gly His Lys
            100                 105                 110

Ala Ser Phe Cys Leu Glu Asp Thr Glu Cys Gly Asp Ile Gln Lys
            115                 120                 125

Asn Tyr Glu Cys Ala Asn Phe Gly Asp Gln Gly Ile Thr Met Gly Cys
    130                 135                 140

Trp Asp Met Tyr Arg His Asp Ile Asp Cys Gln Trp Val Asp Ile Thr
145                 150                 155                 160

Asp Val Pro Pro Gly Asp Tyr Leu Phe Gln Val Val Ile Asn Pro Asn
                165                 170                 175

Phe Glu Val Ala Glu Ser Asp Tyr Ser Asn Asn Ile Met Lys Cys Arg
            180                 185                 190

Ser Arg Tyr Asp Gly His Arg Ile Trp Met Tyr Asn Cys His Ile Gly
            195                 200                 205

Gly Ser
    210

<210> SEQ ID NO 18
<211> LENGTH: 660
<212> TYPE: DNA
<213> ORGANISM: Artificial Sequence
<220> FEATURE:
<223> OTHER INFORMATION: Northern blot probe consisted of nucleotides
      1-660 of the LOXL2 cDNA

<400> SEQUENCE: 18
atggagaggc ctctgtgctc ccacctctgc agctgcctgg ctatgctggc cctcctgtcc      60
cccctgagcc tggcacagta tgacagctgg ccccattacc ccgagtactt ccagcaaccg     120
gctcctgagt atcaccagcc caggccccc gccaacgtgg ccaagattca gctgcgcctg     180
gctgggcaga gaggaagca gcgagggc cgggtggagg tgtactatga tggccagtgg      240
ggcaccgtgt gcgatgacga cttctccatc cacgctgccc acgtcgtctg ccgggagctg     300
ggctatgtgg aggccaagtc ctggactgcc agctcctcct acggcaaggg agaagggccc     360
atctggttag acaatctcca ctgtactggc aacgaggcga cccttgcagc atgcaccctcc    420 aatggctggg gcgtcactga ctgcaagcac acggaggatg tcggtgtggt gtgcagcgac     480
aaaaggattc ctgggttcaa atttgacaat tcgttgatca accagataga gaacctgaat     540
atccaggtgg aggacattcg gattcgagcc atcctctcaa cctaccgcaa gcgcacccca     600
gtgatggagg gctacgtgga ggtgaaggag ggcaagacct ggaagcagat ctgtgacaag     660

<210> SEQ ID NO 19
<211> LENGTH: 530
<212> TYPE: DNA
<213> ORGANISM: Artificial Sequence
<220> FEATURE:
<223> OTHER INFORMATION: Northern blot probe consisted of nucleotides
      1061-1590 of the LOXL3 cDNA

<400> SEQUENCE: 19
gagaagctct gagtggcgct cgcatggggc agggcatggg tgctatccac ctgagtgaag      60
```

```
ttcgctgctc tggacaggag ctctccctct ggaagtgccc ccacaagaac atcacagctg    120
aggattgttc acatagccag gatgccgggg tccggtgcaa cctaccttac actggggcag    180
agaccaggat ccgactcagt gggggccgca gccaacatga ggggcgagtc gaggtgcaaa    240 taggggggacc tgggcccctt cgctggggcc tcatctgtgg ggatgactgg ggaccctgg    300 aggccatggt ggcctgtagg caactgggtc tgggctacgc caaccacggc ctgcaggaga    360
cctggtactg ggactctggg aatataacag aggtggtgat gagtggagtg cgctgcacag    420
ggactgagct gtccctggat cagtgtgccc atcatggcac ccacatcacc tgcaagagga    480
cagggacccg cttcactgct ggagtcatct gttctgagac tgcatcagat              530
```

```
<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
gaaggagaca tccagaagaa t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
cgattactcc aacaacatca t                                              21

<210> SEQ ID NO 22
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 22
ccggccagat agagaacctg aatatctcga gatattcagg ttctctatct ggtttttg     58

<210> SEQ ID NO 23
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 23
ccggcctggg ttcaaatttg acaatctcga gattgtcaaa tttgaaccca ggtttttg     58

<210> SEQ ID NO 24
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 24
ccggcgatta ctccaacaac atcatctcga gatgatgttg ttggagtaat cgtttttg     58

<210> SEQ ID NO 25
<211> LENGTH: 58
```

```
<212> TYPE: DNA
<213> ORGANISM: Artificial Sequence
<220> FEATURE:
<223> OTHER INFORMATION: Synthetic oligonucleotide

<400> SEQUENCE: 25
ccgggagagg acatacaata ccaaactcga gtttggtatt gtatgtcctc tcttttg          58

<210> SEQ ID NO 26
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 26
ccgggaagga gacatccaga agaatctcga gattcttctg gatgtctcct tcttttg          58

<210> SEQ ID NO 27
<211> LENGTH: 31
<212> TYPE: DNA
<213> ORGANISM: Artificial Sequence
<220> FEATURE:
<223> OTHER INFORMATION: Synthetic primer

<400> SEQUENCE: 27
cgccggaatt cgctcacagt accagcctca g                                     31

<210> SEQ ID NO 28
<211> LENGTH: 32
<212> TYPE: DNA
<213> ORGANISM: Artificial Sequence
<220> FEATURE:
<223> OTHER INFORMATION: Synthetic primer

<400> SEQUENCE: 28
ccaaaactgc aggtagtagt tgtaataagg gt                                    32

<210> SEQ ID NO 29
<211> LENGTH: 31
<212> TYPE: DNA
<213> ORGANISM: Artificial Sequence
<220> FEATURE:
<223> OTHER INFORMATION: Synthetic primer

<400> SEQUENCE: 29
cgccggaatt cggtcatcta cccctaccag c                                     31

<210> SEQ ID NO 30
<211> LENGTH: 30
<212> TYPE: DNA
<213> ORGANISM: Artificial Sequence
<220> FEATURE:
<223> OTHER INFORMATION: Synthetic primer

<400> SEQUENCE: 30
ctagtctaga acatagttgg ggtctgggac                                       30
```

COMPOSITIONS AND METHODS FOR TREATING TUMORS, FIBROSIS, AND PULMONARY ALVEOLAR PROTEINOSIS

CROSS REFERENCE TO RELATED APPLICATIONS

This application is a divisional of U.S. patent application Ser. No. 12/669,035 filed Jun. 25, 2010, now allowed, which is a national phase application of PCT/IL2008/000985 having an international filing date of Jul. 15, 2008, which claims the benefit of Israeli Patent Application No. 184627, filed Jul. 15, 2007. The entire contents of these applications are incorporated herein by this reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 246102007910Seqlist.txt, date recorded: Sep. 11, 2012, size: 44,631 bytes).

BACKGROUND

Lysyl oxidase (LO or LOX) is a copper containing amine oxidase that oxidizes primary amine substrates to reactive aldehydes. LOX catalyzes oxidative deamination of peptidyl lysine and hydroxylysine residues in collagens, and peptidyl lysine residues in elastin, and aids in the formation of the extracellular matrix. The resulting peptidyl adelydes typically condense and undergo oxidation reactions to form the lysine-derived covalent cross-links required for the normal structural integrity of the extracellular matrix. Hydrogen peroxide ($H_2O_2$) and ammonium are usually released in quantities stoichiometric with the peptidyl aldehyde product. LOX can oxidize certain lysine residues in collagen and elastin outside of the cell; however, it may also act intracellularly, where it may regulate gene expression. In addition, LOX can induce chemotaxis of monocytes, fibroblasts and smooth muscle cells. LOX itself can be induced by a number of growth factors and steroids such as TGF-β, TNF-α and interferon (Csiszar, *Prog. Nucl. Acid Res.* 70:1-32 (2001)). LOX has also been implicated in diverse biological functions such as developmental regulation, tumor suppression, cell motility, and cellular senescence. The diverse role of LOX and its recently discovered amino oxidase family members, lysyl oxidase related or lysyl oxidase-like proteins (LOR or LOXL), may play important roles with respect to their intracellular and extracellular localization.

The expression or implication of LOX and LOXL in diseases may also vary. This may be due to a number of reasons, such as the difference in tissue distribution, processing, domains, regulation of activity, as well as other differences between the proteins. For example, LOX and LOXL are implicated in fibrotic diseases as both LOX and LOXL are highly expressed in myo-fibroblasts around fibrotic areas (Kagen, *Pathol. Res. Pract.* 190:910-919 (1994); Murawaki et al., *Hepatology* 14:1167-1173 (1991); Siegel et al., *Proc. Natl. Acad. Sci.* USA 75: 2945-2949 (1978); Jourdan Le-Saux et al., *Biochem. Biophys. Res. Comm.* 199:587-592 (1994); Kim et al., *J. Cell Biochem.* 72:181-188 (1999)). LOX and the various LOXL are also implicated in a number of cancers. For example, LOXL and LOXL4 have been shown to be epigenetically silenced and can inhibit ras/extracellular signal-regulated kinase signaling pathway in human bladder cancer (Wu et al., *Cancer Res.* 67:4123-4129 (2007)). Others have shown selective upregulation and amplification of the LOXL4 gene in head and neck squamous cell carcinoma (Gorough et al., *J. Pathol.* 212:74-82 (2007)). LOX and LOXL2 have also been implicated in a number of tumors, such as colon and esophageal cancers (Csiszar, *Prog. Nucl. Acid Res.* 70:1-32 (2001)). In breast cancer, LOX and the LOXL family members have been linked to cancer (Kirschmann et al., *Cancer Res.* 62:448-4483 (2002)).

Thus, there is a need for compositions and methods to modulate LOX and LOXL activity. One such method is through the use of RNA interference (RNAi). RNAi refers to methods of sequence-specific post-transcriptional gene silencing which is mediated by a double-stranded RNA (dsRNA) called a short interfering RNA (siRNA). RNAi is an endogenous mechanism that uses small noncoding RNAs to silence gene expression. When an siRNA is introduced into a cell, it binds to the endogenous RNAi machinery to alter the level of mRNA containing complementary sequences with high specificity. The RNAi response involves an endonuclease complex known as the RNA-induced silencing complex (RISC), which mediates cleavage of a single-stranded RNA complementary to the antisense strand of the siRNA duplex. Cleavage of the target RNA takes place in the middle of the region complementary to the antisense strand of the siRNA duplex (Elbashir et al., *Genes Dev.* 15:188-200, (2001)).

As a result, there is a need for compositions to modulate LOX and LOXL, such as through the use of RNAi. Methods for using such compositions to treat and diagnose conditions are also needed. The present disclosure addresses these needs and provides other advantages as well.

SUMMARY

The present disclosure provides pharmaceutical compositions and methods useful for modulating angiogenesis and fibrosis, and for treating cancer, by inhibiting metastasis and tumors in a subject, such as primary tumors. Moreover, the expression of LOXL2 is correlated with pulmonary alveolar proteinosis and as such can be used for accurate diagnosis and treatment of pulmonary alveolar proteinosis (PAP).

In one aspect, the present disclosure provides an isolated polynucleotide comprising a first sequence hybridizable to a polynucleotide sequence encoding LOXL2 or SEQ ID NO. 2, a second sequence complementary to the first sequence, and a linking sequence that joins the first sequence to the second sequence. The linking sequence can form a hairpin loop structure. The first sequence can comprise SEQ ID NO. 20 or 21. Also provided is an isolated polynucleotide comprising SEQ ID NO. 20 or 21. The isolated polynucleotide can be at least twice the length of SEQ ID NO. 20 or 21. The isolated polynucleotide comprising SEQ ID NO. 20 may further comprise a second sequence complementary to it. Alternatively, the isolated polynucleotide comprising SEQ ID NO. 21 may further comprise a second sequence complementary to it. The isolated polynucleotides comprising SEQ ID NO. 20 or 21 may also comprise a hairpin loop structure. Further provided are expression vectors comprising the isolated polynucleotides as well as host cells comprising the expression vectors.

In another aspect, pharmaceutical compositions comprising a polynucleotide comprising a first sequence hybridizable to a polynucleotide sequence encoding LOXL2 or SEQ ID NO. 2, a second sequence complementary to the first sequence, and a linking sequence that joins the first sequence to the second sequence; and, a pharmaceutical excipient, are provided. Also provided are pharmaceutical compositions comprising a polynucleotide comprising SEQ ID NO. 20 or 21; and, a pharmaceutical excipient.

The present disclosure also provides methods of administering the compositions described herein. Methods for inhibiting primary tumor growth, metastasis, fibrosis, or angiogenesis in a subject are also disclosed. The methods can comprise administering to the subject an effective amount of a polynucleotide to inhibit primary tumor growth, metastasis, fibrosis, or angiogenesis in the subject. The polynucleotide can comprise a first sequence hybridizable to a polynucleotide sequence encoding LOXL2 or SEQ ID NO. 2, a second sequence complementary to the first sequence, and a linking sequence that joins the first sequence to the second sequence. The polynucleotide can comprise a linking sequence that forms a hairpin loop structure. The first sequence can comprise SEQ ID NO. 20 or 21. The methods can also encompass administering to a subject a polynucleotide comprising SEQ ID NO. 20 or 21 to inhibit primary tumor growth, metastasis, fibrosis, or angiogenesis in the subject.

Methods for treating PAP in a subject are also provided. The present disclosure provides methods comprising administering to the subject an effective amount of an agent to inhibit PAP, wherein the agent modulates the expression or activity of a lysyl oxidase or lysyl oxidase like protein. Methods for detecting PAP in a subject are also provided, wherein the subject is administered an agent that detects the expression or activity of a lysyl oxidase or lysyl oxidase like protein, wherein the expression or activity is used to diagnose PAP in the subject. The lysyl oxidase level or activity may be that of LOXL2, LOXL3, or both, and the agent used to treat or diagnose PAP can be an antibody, a small molecule, antisense molecule, ribozyme, DNAzyme, triple helix forming oligonucleotides, siRNA, or shRNA. The agent may be an inhibitor of lysyl oxidase or lysyl oxidase like protein, such as LOXL2, LOXL3, or both.

INCORPORATION BY REFERENCE

All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

BRIEF DESCRIPTION OF THE DRAWINGS

A better understanding of the features and advantages of the present invention may be obtained by reference to the following detailed description that sets forth illustrative embodiments, in which the principles of the invention are utilized, and the accompanying drawings of which:

FIG. 1 illustrates LOXL2 shRNA sequences. Each sequence forms a hairpin as the underlined sequences in each are sense/antisense strands. The shRNA are expressed using the pLKO.1-puro vector (available from Sigma) to allow for transient or stable transfection of the shRNA as well as production of lentiviral particles.

DETAILED DESCRIPTION

Figure 2:
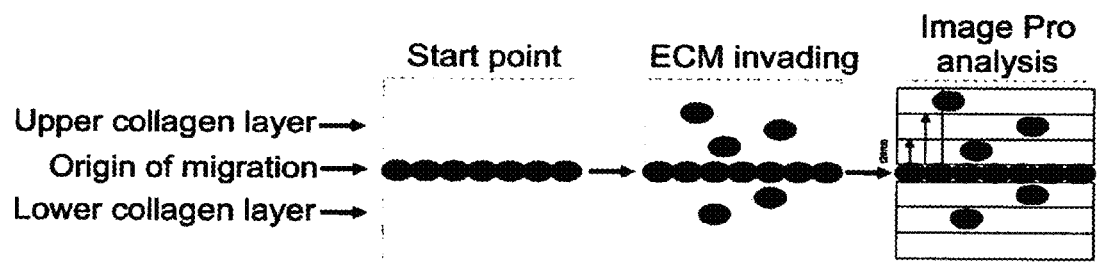
FIG. 2 is a schematic illustrating the tumor invasion assay.

The principles and operation of the present disclosure may be better understood with reference to the drawings and accompanying description. It is to be understood that disclosure is not limited in its application to the details of construction and the arrangement of the components set forth in the following description or illustrated in the drawings described in the Examples section. The disclosure is capable of other embodiments or of being practiced or carried out in various ways. Also, it is to be understood that the phraseology and terminology employed herein is for the purpose of description and should not be regarded as limiting.

The present disclosure provides pharmaceutical compositions and methods that can be used to modulate angiogenesis and to inhibit tumor growth, tumor invasiveness and tumor fibrosis. For example, the present disclosure can be used to suppress tumor growth and metastasis as well as to treat and diagnose disorders such as, for example, arthritis, diabetic retinopathy, psoriasis, vasculitis and PAP.

The innovative methods and compositions described include the use of an inhibitor of LOX or LOXL, such as agents that inhibit LOXL2. An example of LOX or LOXL include the enzyme having an amino acid sequence substantially identical to a polypeptide expressed or translated from one of the following sequences: EMBL/GenBank accessions: M94054; AAA59525.1—mRNA; S45875; AAB23549.1—mRNA; S78694; AAB21243.1—mRNA; AF039291; AAD02130.1—mRNA; BC074820; AAH74820.1—mRNA; BC074872; AAH74872.1—mRNA; M84150; AAA59541.1—Genomic DNA. Particular examples of LOXL are described in Molnar et al., *Biochim Biophys Acta.* 1647: 220-24 (2003); Csiszar, *Prog. Nucl. Acid Res.* 70:1-32 (2001); and in WO 01/83702. (It is noted that in these 3 publications, "LOXL1" was referred to as "LOXL" whereas in the present invention "LOXL" is referred to a lysyl oxidase-like protein in general, not just LOXL1.) These enzymes include LOXL1, encoded by mRNA deposited at GenBank/EMBL BC015090; AAH15090.1; LOXL2, encoded by mRNA deposited at GenBank/EMBL U89942; LOXL3, encoded by mRNA deposited at GenBank/EMBL AF282619; AAK51671.1; and LOXL4, encoded by mRNA deposited at GenBank/EMBL AF338441; AAK71934.1.

LOX or LOXL also encompasses a functional fragment or a derivative that still substantially retains its enzymatic activity catalyzing the deamination of lysyl residues. Typically, a functional fragment or derivative retains at least 50% of its lysyl oxidase activity. A functional fragment or derivative can retain at least 60%, 70%, 80%, 90%, 95%, 99% or 100% of its lysyl oxidase activity. A LOX or LOXL can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity.

Inhibitors used may include inhibitors of the lysyl oxidase family of enzymes which catalyze the formation of covalent crosslinks between lysine residues on adjacent collagen or elastin fibrils. At least five different lysyl oxidases are known to exist in both humans and mice, LOX and four LOX related, or LOX-like proteins: LOXL1 (or LOL), LOXL2 (or LOR-1), LOXL3 (or LOR-2), and LOXL4 (or Lox-C). The five forms of lysyl oxidases reside on five different chromosomes. These family members show some overlap in structure and function, but appear to have distinct functions as well. For example, LOX appears to be lethal at parturition in mice (Hornstra et al., *J. Biol. Chem.* 278:14387-14393 (2003)), whereas LOXL deficiency causes no severe developmental phenotype (Bronson et al., *Neurosci. Lett.* 390:118-122 (2005)). The lysyl oxidase family includes four genes, such as those with SEQ ID NOs. 1, 4, 5, or 7, or enzymes with the amino acid sequences in SEQ ID NOs: 2, 3, 6, 8, or 9.

LOX has highly conserved protein domains, conserved in several species including human, mouse, rat, chicken, fish and *Drosophila*. The human LOX family has a highly conserved C-terminal region containing the 205 amino acid LOX catalytic domain. The conserved region contains the copper binding (Cu), cytokine receptor like domain (CRL), and the lysyl-tyrosylquinone cofactor site (LTQ). Twelve cysteine residues are also similarly conserved, two being present in the prepropeptide region and ten in the catalytically active processed form of LOX (Csiszar, *Prog. Nucl. Acid Res.* 70:1-32 (2001)).

The prepropeptide region of LOX contains a signal peptide that is cleaved. The cleavage site is predicted to be between Cys21-Ala22, generating a 16 (or 21) signal sequence and a 48 kDa amino acid propeptide form of LOX, which is, without being bound by theory, still inactive. Without being limited by theory, the propeptide is N-glycosylated during passage through the Golgi yielding a 50 kDa inactive proenzyme that is secreted into the extracellular environment where the proenzyme, or propeptide, is cleaved between Gly168-Asp169 by a metalloendoprotease, a procollagen C-proteinase, which are products of the Bmp1, Tll1 and Tll2 genes. BMP I (bone morphogenetic protein I) is a procollagen C-proteinase that processes the propeptide to yield a functional 30 kDa enzyme and an 18 kDa propeptide. The sequence coding for the propeptide is typically moderately (approximately 60-70%) conserved, whereas the sequence coding for the C-terminal 30 kDa region of the proenzyme in which the active site is located is usually highly conserved (approximately 95%). (Kagan and Li, *J. Cell. Biochem.* 88:660-672 (2003); Kagan et al., *J. Cell Biochem.* 59:329-38 (1995)). The N-glycosyl units are usually subsequently removed.

Similar potential signal peptides have been predicted at the amino termini of LOXL, LOXL2, LOXL3, and LOXL4. The predicted signal cleavage sites are between Gly25-Gln26 for LOXL, between Ala25-Gln26, for LOXL2, and between Gly25-Ser26 for LOXL3. The consensus for BMP-1 cleavage in procollagens and pro-LOX is between Ala/Gly-Asp, and often followed by an acidic or charged residue. A potential cleavage site to generate active LOXL is Gly303-Asp304, however, it is then followed by an atypical Pro. LOXL3 also has a potential cleavage site at Gly44y-Asp448, which is followed by an Asp, processing at this site may yield an active peptide of similar size to active LOX. A potential cleavage site of BMP-1 was also identified within LOXL4, at residues Ala569-Asp570 (Kim et al., *J. Biol. Chem.* 278:52071-52074

(2003)). LOXL2 protein may also be processed analogously to the other LOX family members.

A feature that may differ amongst the lysyl oxidases and lysyl oxidase like proteins is the scavenger receptor cysteine rich (SRCR) domains. LOX and LOXL appear to lack SRCR domains, whereas LOXL2, LOXL3, and LOXL4 each have four SRCR domains at the N-terminus. SRCR domains mediate ligand binding in a number of secreted and receptor proteins (Hoheneste et al., *Nat. Struct. Biol.* 6: 228-232 (1999); Sasaki et al., *EMBO J.* 17:1606-1613 (1998)). Another domain that appears to be unique to LOXL is the presence of a proline rich domain (Molnar et al., *Biochimica Biophsyica Acta* 1647: 220-224 (2003)).

Figure 12:
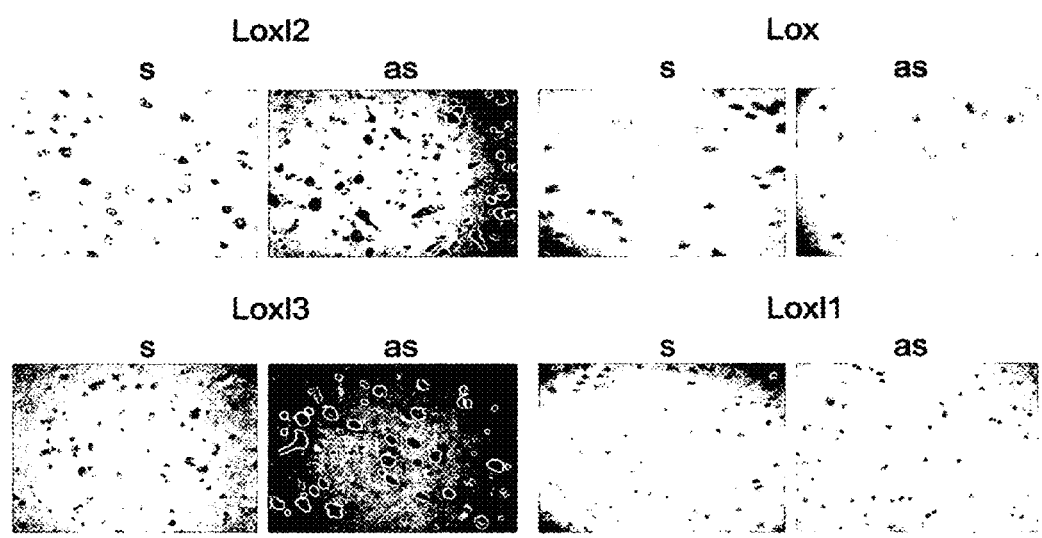
FIG. 12 illustrates expression of LOXL2 and LOXL3 in neuronal cells of the central nervous system (CNS). In-situ hybridization on tissue sections from normal human brain cortex was performed using probes directed at LOX, LOXL1, LOXL2, or LOXL3. S=sense, as=antisense.

Tissue distribution may also differ amongst LOX and the various LOXL. For example, as shown in FIG. 12, LOXL2 and LOXL3 are highly expressed in neuronal cells, whereas LOX and LOXL1 are not. Thus, in one aspect, the present disclosure encompasses modulating expression of LOX or LOXL in the CNS, such as in the brain, or more specifically in neuronal cells.

Each member of the LOX family of enzymes includes a highly conserved lysyl oxidase domain, the activity of which is highly dependent on the presence of copper. Removal of copper from tumor tissues leads to inhibition of angiogenesis (Rabinovitz, *J. Natl. Cancer Inst.* 91:1689-1690 (1999); Yoshida et al., *Neurosurgery* 37: 287-292 (1995)). This further substantiates the role of the lysyl oxidase family of enzymes in angiogenesis as, without being bound by theory, removal of copper leads to inhibition of lysyl oxidases.

Further support to the angiogenic activity of lysyl oxidases is provided by the PF4-LOXL2 binding assays. PF4 is an inhibitor of angiogenesis. As such, the anti-angiogenic activity exhibited by PF4 may be, without being limited by theory, effected through LOXL2 inhibition, which is highly expressed in the endothelial cells lining blood vessels. Thus according to one aspect of the present disclosure, methods of modulating angiogenesis are provided.

Angiogenesis

In an adult, formation of new blood vessels in normal or diseased tissues is typically regulated by two processes, recapitulated vasculogenesis (the transformation of pre-existing arterioles into small muscular arteries) and angiogenesis, the sprouting of existing blood vessels (which occurs both in the embryo and in the adult). Furthermore, LOXL2 expression is induced under hypoxic conditions (FIG. 10), as angiogenesis is thought to be spurred in cancers to overcome hypoxic conditions.

The process of angiogenesis is regulated by biomechanical and biochemical stimuli. Angiogenic factors such as vascular endothelial growth factor (VEGF) and basic fibroblast growth factor (bFGF) are released by vascular cells, macrophages, and cells surrounding blood vessels. These angiogenic factors activate specific proteases that are involved in degradation of the basement membrane. As a result of this degradation, vascular cells migrate and proliferate thus leading to new blood vessel formation. Peri-endothelial cells, such as pericytes in the capillaries, smooth muscle cells in larger vessels and cardiac myocytes in the heart are recruited to provide maintenance and modulatory functions to the forming vessel.

The establishment and remodeling of blood vessels is controlled by paracrine signals, many of which are mediated by protein ligands which modulate the activity of transmembrane tyrosine kinase receptors. Among these molecules are vascular endothelial growth factor (VEGF) and its receptor families (VEGFR-1, VEGFR-2, neuropilin-1 and neuropilin-2), Angiopoietins 1-4 (Ang-1, Ang-2 etc.) and their respective receptors (Tie-1 and Tie-2), basic fibroblast growth factor (bFGF), platelet derived growth factor (PDGF), and transforming growth factor β (TGF-β).

The growth of solid tumors is limited by the availability of nutrients and oxygen. When cells within solid tumors start to produce angiogenic factors or when the levels of angiogenesis inhibitors decline, the balance between anti-angiogenic and angiogenic influences is perturbed, initiating the growth of new blood vessels from the existing vascular bed into the tumor. This event in tumor progression is known as the angiogenic switch. Inhibitors of tumor angiogenesis are able to inhibit tumor growth in mice, in some cases, it appears to completely inhibit tumor growth and also inhibit tumor metastasis, a process that relies upon close contact between the vasculature and tumor cells. Angiogenesis plays an important role in the progression of breast cancer.

Such findings have prompted the use of known anti-angiogenic factors in breast cancer therapy (Klauber et al., *Cancer Res.* 57:81-86 (1997); Harris et al., *Breast Cancer Res. Treat.* 38, 97-108 (1996); Weinstatsaslow et al., *Cancer Res.* 54; 6504-6511 (1994)). During the past decade several novel inhibitors of angiogenesis have been isolated including inhibitors of VEGF signaling (Neufeld et al., *FASEB J.* 13:9-22 (1999)) and inhibitors of processes which lead to the maturation and stabilization of new blood vessels. Anti-integrin antibodies have been used as inhibitors of blood vessel maturation (Brooks et al., *Cell* 79:1157-1164 (1994); Brooks et al., *Cell* 92:391-400 (1998)).

Although several anti-angiogenic drugs are now available commercially, the anti-angiogenic mechanisms of most of these drugs (e.g., angiostatin and endostatin) remain unclear (O'Reilly et al., *Cell* 88: 277-285 (1997); O'Reilly et al., *Nature Med.* 2:689-692 (1996)). Since angiogenesis can be initiated by many (possibly compensatory) angiogenic factors, anti-angiogenic factors which target later processes in the angiogenic response such as vessel maturation or a combination of anti-angiogenic factors are likely to be effective in arresting vessel formation.

Platelet factor-4 (PF4) is an anti-angiogenic protein normally sequestered in platelets (Tanaka et al., *Nature Med.* 3:437-442 (1997); Malone et al., *Science* 247: 77-79 (1990); Neufeld et al., *The Cytokine Reference: A compendium of cytokines and other mediators of host defence* (Oppenheim, J. J. and Feldmann, M. eds) Academic Press (2000)). PF4 inhibits angiogenesis using poorly defined mechanisms (Gengrinovitch et al., *J. Biol. Chem.* 270:15059-15065 (1995); Brown and Parish, *Biochemistry* 33:13918-13927 (1994); .Gupta and Singh, *J. Cell Biol.* 127:1121-1127 (1994); Watson et al., *J. Clin. Invest.* 94: 261-268 (1994)). It was previously speculated that PF4 binds to cell surface heparan-sulfate proteoglycans and in this manner inhibits the activity of angiogenic growth factors such as basic fibroblast growth factor (Watson et al., *J. Clin. Invest.* 94: 261-268 (1994)).

For example, the compositions and methods described in the present disclosure can be used to suppress tumor growth by inhibiting angiogenesis, or by directly inhibiting tumor growth (such as primary tumor growth), suppressing metastasis, as well as to treat and diagnose disorders such as, for example, arthritis, diabetic retinopathy, psoriasis and vasculitis and primary pulmonary alveolar proteinosis.

Metastatic and Primary Tumors

The prevention, reduction, and diagnosis of tumors are important in the prevention and treatment of cancer. The transition from a localized tumor to an invasive and metastatic tumor represents a landmark in the development of malignant disease, since it is usually associated with a markedly worse prognosis. The understanding of the processes that govern this transition is therefore of prime importance, and LOX and LOXL roles in these processes can be used to not only further understanding of this process, but also be used to treat, prevent, or diagnosis primary and metastatic tumors.

Figure 3A:
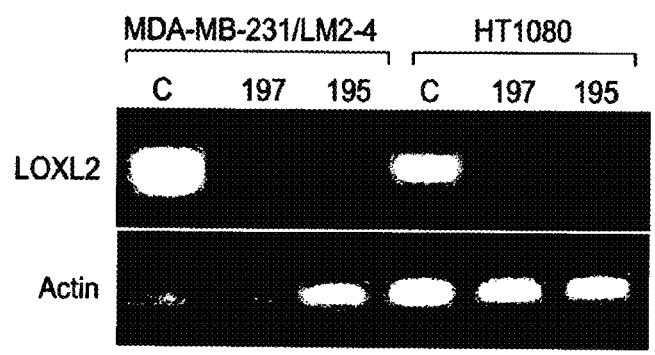
FIG. 3 illustrates the expression of LOXL2 in (A) MDA-MDB 231/LM2-4 and HT1080 cancer cells and in (B) MDA-MB 231 breast cancer and YU/PAC2 melanoma cells, infected with lentiviral vectors directing expression of 195 or 197 LOXL2 specific shRNA (also referred to as sh.Loxl2.195 or sh.Loxl2.197, respectively)
Figure 3B:
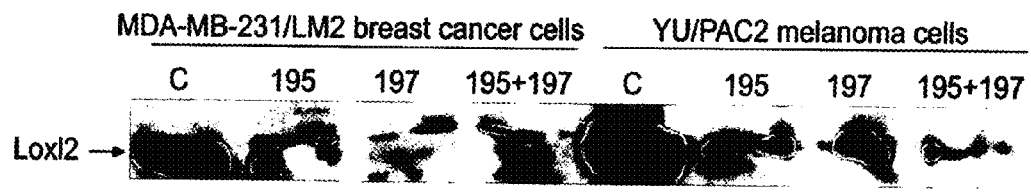
Figure 4:
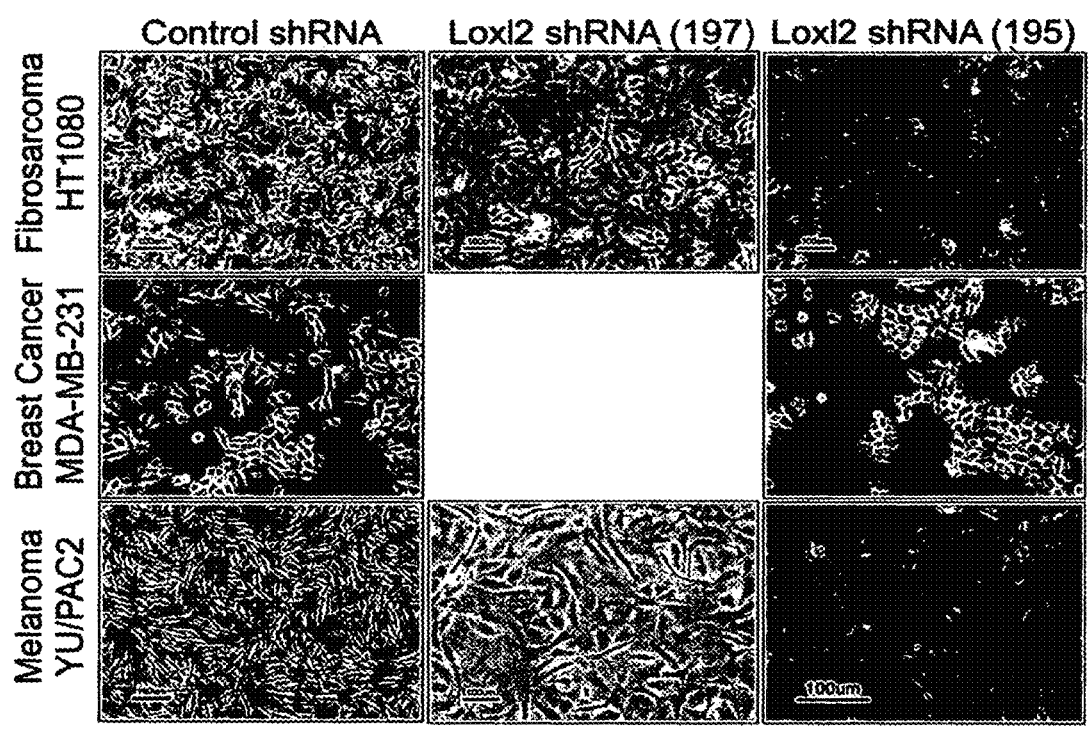
FIG. 4 is a microphotograph illustrating the morphological shift in cells infected with lentiviral vectors directing expression of sh.Loxl2.195 or sh.Loxl2.197.
Figure 5A:
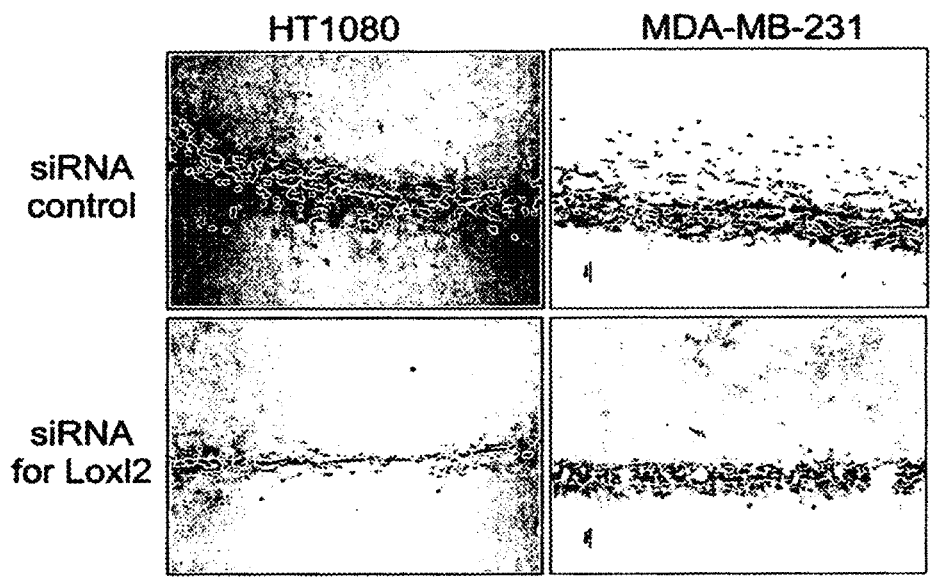
FIG. 5 is (A) a microphotograph illustrating the effect of lentiviral vectors directing expression of sh.Loxl2.195 or sh.Loxl2.197 on MDA-MB-231 breast cancer cells and HT1080 fibrosarcoma cells in the tumor invasion assay. (B) is a Western blot showing the knockdown of LOXL2 expression and (C) show the number of invading cells per field.
Figure 5B:
Figure 7A:
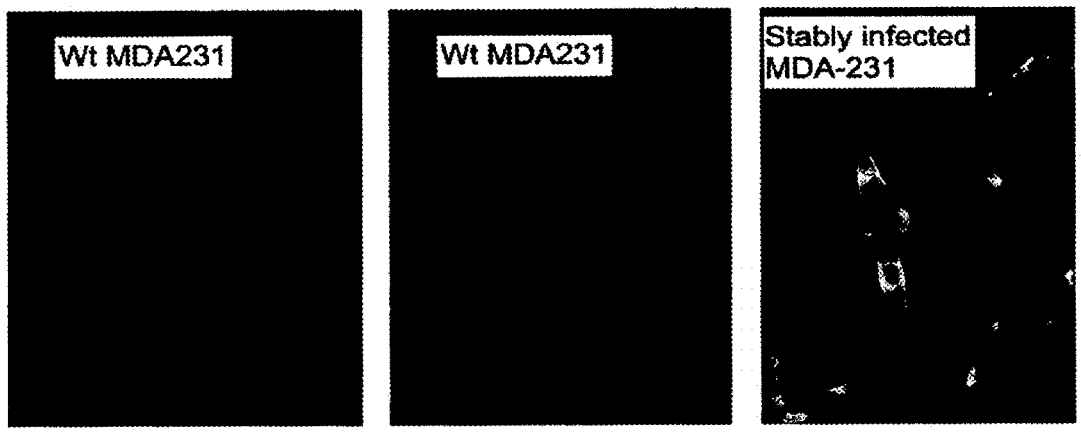
FIG. 7 illustrates rhodamine phalloidin staining of MDA-231 cells. (A) Wild type MDA-231 cells and control-infected lentiviral stable MDA-231 cells with phalloidin staining of F-actin reveal long fibrils typical of a cell that has undergone epithelial-mesenchymal transition (EMT). (B) MDA-231 cells infected with sh.Loxl2.195 are depleted for LOXL2 and revealed a "rim" effect near the cell membrane, more typical of a normal epithelial cell.
Figure 7B:
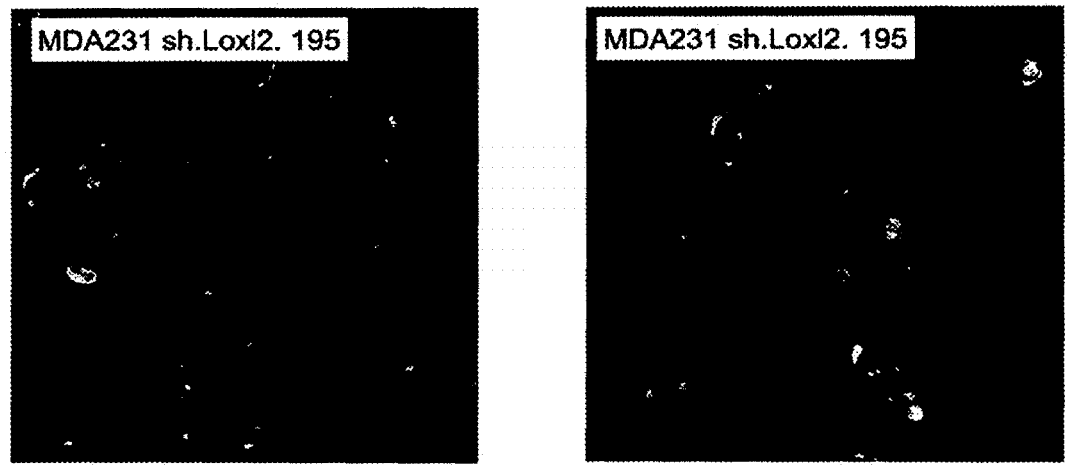
Figure 8A:
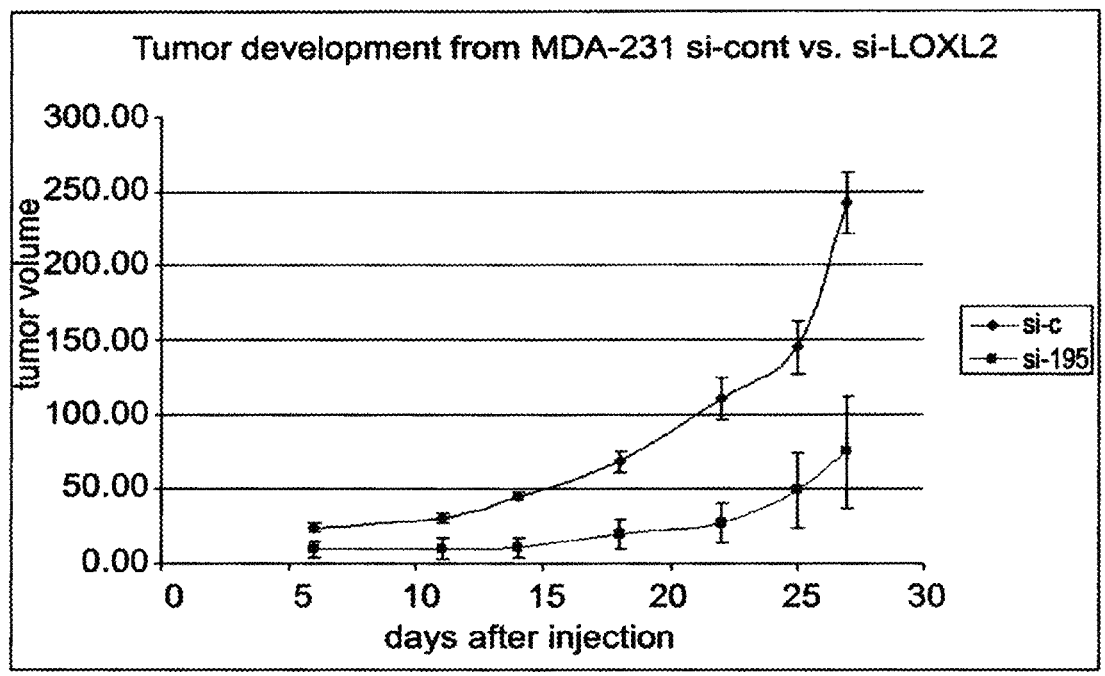
FIG. 8 illustrates primary tumor development in mice injected with MDA-231 si-control (si-c) or sh.Loxl2.195 (si-195) cells. MDA-231 cells were infected with control shRNA encoding lentivirus or lentivirus vector expressing sh.Loxl2.195. The cells were selected with puromycin and Loxl2 expression determined prior to injection into the mammary fat pads of balb/c nu/nu female mice. (A) Tumor volume was measured 6, 11, 14, 18, 22, 25, and 27 days after injection. (B) illustrates tumor weight from MDA-231 si-cont vs. sh.Loxl2.195 (si-195) mice 27 days after injection.
Figure 8B:
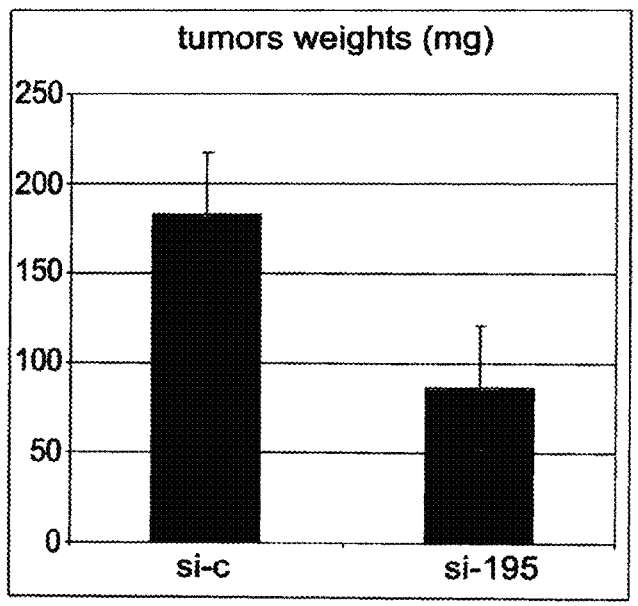

For example, LOXL2 expression can be decreased in breast cancer cells, melanoma cells and fibrosarcoma cells using shRNA or siRNA (FIGS. 3, 5B). Administration of shRNA or siRNA targeting LOXL2 led to an EMT to MET like transition (FIG. 4, FIG. 7) as well as decrease in cell invasion (FIG. 5), further supporting the role of LOXL2 in tumor metastasis, and by modulating LOXL2 expression can aid in inhibiting metastatic activity. Inhibition of LOXL2 can also be used in inhibiting tumor growth and reducing primary tumors. Tumor growth inhibition can be preventative. Alternatively, inhibition of primary tumor growth can be a reduction of tumor mass, for example, tumor mass can be reduced compared to size or volume of tumor when initially detected. The inhibition can be in the rate of growth of the primary tumor, for example, the primary tumor mass or volume increases at a slower rate in comparison to a subject not treated with compositions disclosed herein, for example, as shown in FIG. 8.

Breast Cancer

In breast cancer, the transition from a localized to an invasive/metastatic tumor is associated in many cases with the formation of fibrotic foci and desmoplasia, which is the presence of unusually dense collagenous stroma, within the primary tumor (Colpaert et al., *Am. J. Surg. Pathol.* 25, 1557 (2001); Hasebe et al., *Pathology International* 50: 263-272 (2000)). A similar correlation may exist in other types of cancers such as colon and pancreatic cancers (Nishimura et al., *Virchows Arch.* 433:517-522 (1998); Ellenrieder et al., *Int. J. Cancer* 85:14-20 (2000)). These observations represent apparent paradoxes at first glance, since invasiveness has long been associated with the destruction of extracellular matrix by extracellular matrix degrading enzymes like metalo-proteases (Stamenkovic, *Semin. Cancer Biol.* 10:415-433 (2000); Duffy et al., *Breast Cancer Res.* 2: 252-257 (2000)) and heparanase (Vlodavsky and Friedmann, *J. Clin. Invest* 108:341-347 (2001)). However, it is possible that deposition of excess extracellular matrix may stimulate in turn expression of matrix degrading enzymes that will contribute under certain circumstances to tumor invasion. In fact, there is some evidence that an increase in extracellular matrix deposition can indeed influence the production of extracellular matrix degrading enzymes (Schuppan et al., *Semin. Liver Dis.* 21:351-372 (2001); Swada et al., *Int. J. Oncol.* 19:65-70 (2001)).

Colon Cancer

Cancer of the gastrointestinal (GI) tract, especially colon cancer, is a highly treatable and often a curable disease when localized to the bowel. Surgery is the primary treatment and results in cure in approximately 50% of patients. Recurrence following surgery is a major problem and often is the ultimate cause of death. Nearly all cases of colorectal cancer arise from adenomatous polyps, some of which mature into large polyps, undergo abnormal growth and development, and ultimately progress into cancer. This progression would appear to take at least 10 years in most patients, rendering it a readily treatable form of cancer if diagnosed early, when the cancer is localized.

The standard procedures currently used for establishing a definitive diagnosis for a GI tract cancer include barium studies, endoscopy, biopsy, and computed tomography (Brennan et al., *Cancer: Principles and Practice of Oncology*, Fourth Edition, pp. 849-882, Philadelphia, Pa.: J. B. Lippincott Co. (1993)).

The prognosis of colon cancer is typically related to the degree of penetration of the tumor through the bowel wall and the presence or absence of nodal involvement. These two characteristics usually form the basis for staging systems developed for this to disease. Staging is usually performed by a pathologist on tissue sections obtained via biopsy and/or surgery and it aims to determine the anatomic extent of the disease. Accurate staging is critical for predicting patient outcome and providing criteria for designing optimal therapy. Inaccurate staging can result in poor therapeutic decisions and is a major clinical problem in colon cancer.

Primary Alveolar Proteinosis (PAP)

Figure 6:
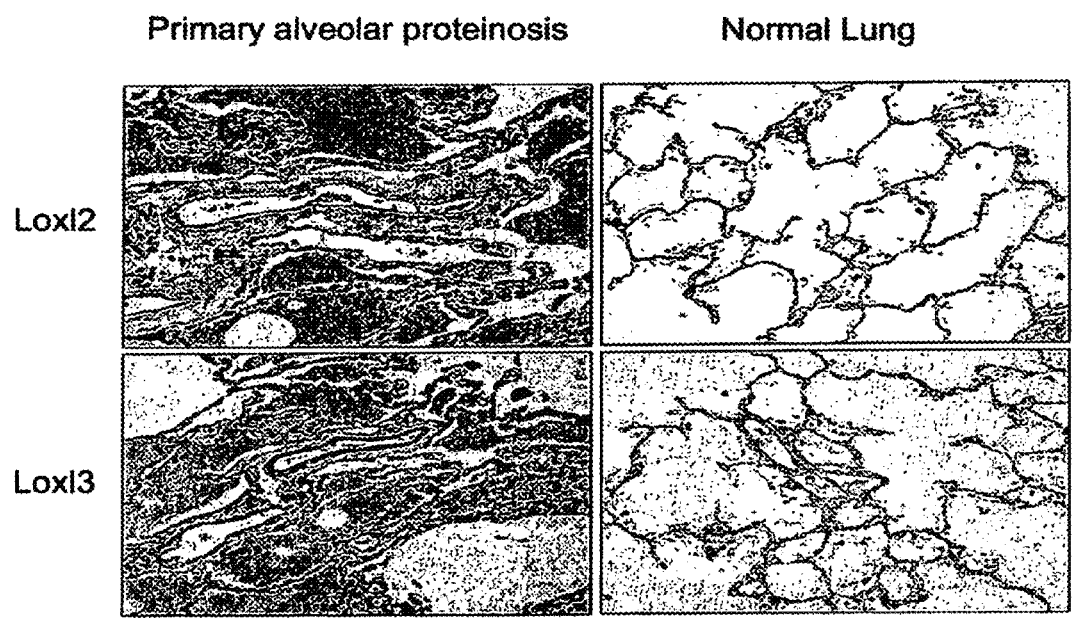
FIG. 6 is a photomicrograph illustrating the expression of LOXL2 and LOXL3 in normal and PAP lung tissue.

PAP is a rare lung disorder of unknown etiology characterized by alveolar filling with floccular material that stains positive using the periodic acid-Schiff (PAS) method and is derived from surfactant phospholipids and protein components. LOXL2 and LOXL3 are likely to have a role in PAP as both are expressed in PAP tissue, but not normal lung tissue (FIG. 6)

Two forms are recognized, (1) primary (idiopathic) and (2) secondary (due to lung infections; hematologic malignancies; and inhalation of mineral dusts such as silica, titanium oxide, aluminum, and insecticides). Incidence of PAP is increased in patients with hematologic malignancies and AIDS, suggesting a relationship with immune dysfunction.

The alveoli in PAP are filled with proteinaceous material, which has been analyzed extensively and determined to be normal surfactant composed of lipids and surfactant-associated proteins A, B, C, and D (SP-A, SP-C, SP-D). Evidence exists of a defect in the homeostatic mechanism of either the production of surfactant or the clearance by alveolar macrophages and the mucociliary elevator. A clear relationship has been demonstrated between PAP and impaired macrophage maturation.

PAP has an estimated prevalence of 1 case per 100,000 population, and mortality rates of as high as 30% within several years of disease onset have been reported previously. The actual mortality rate may be less than 10%. Incidence for males is 4 times higher than for females. Patients are typically 20-50 years old at presentation.

Patients with PAP typically present with a gradual onset of symptoms. As many as 30% of patients are asymptomatic, even with diffuse chest radiograph (CXR) abnormalities. Symptoms can include the following: persistent dry cough (or scant sputum production), progressive dyspnea, fatigue and malaise, weight loss, intermittent low-grade fever and/or night sweats, pleuritic chest pain, cyanosis, and hemoptysis.

The etiology of PAP is unknown. Causes may include inhalation of silica dust (acute silicoproteinosis), exposure to insecticides, aluminum dust, titanium dioxide, and other inorganic dusts, hematologic malignancies, myeloid disorders, lysinuric protein intolerance, HIV infection (AIDS), leflunomide-case report and disease-modifying antirheumatoid arthritis therapy. Differentials may include hypersensitivity pneumonitis, lung cancer, non-small cell lung cancer, oat cell lung cancer (Small Cell), *Pneumocystis carinii* pneumonia, pulmonary edema and cardiogenic sarcoidosis. The diagnosis can be made by lavage, if PAS staining is requested. Therefore, PAP is probably underdiagnosed.

Lung biopsies are classicly used in diagnosing for PAP: Alveoli are filled with nonfoamy material. Transbronchial biopsies are adequate, and open lung biopsy is not required.

Management of PAP depends on the progression of the illness, coexisting infections, and degree of physiological impairment. The standard of care for PAP is mechanical removal of the lipoproteinaceous material by whole-lung lavage, which is often repeated. Historically, patients have been treated with systemic steroids, mucolytics (aerosol), and proteinase (aerosol) without much success. In secondary PAP, appropriate treatment of the underlying cause also is warranted. GM-CSF has been shown to improve PAP in several patients and is being investigated. Congenital PAP responds favorably to lung transplantation.

Lung transplantation is the treatment of choice in patients with congenital PAP and in adult patients with end-stage interstitial fibrosis and cor pulmonale. The major complications are lung infections with *N asteroides*, *Pneumocystis carinii*, and/or *Mycobacterium avium-intracellulare*. Pulmonary fibrosis and/or cor pulmonale also can complicate PAP.

Thus, to increase the accuracy of therapy and the survival rate of PAP patients there is a need to develop accurate methods of diagnosing and treatment of PAP, and the compositions and methods described herein can be used in diagnosing and treating PAP.

Methods and Compositions

The methods described herein are effected by administering to a subject a pharmaceutical compositions comprising a molecule capable of modifying a tissue level and/or activity of at least one type of LOX to thereby modulate angiogenesis in the mammalian tissue. Administration may be into a mammalian tissue. Modifying the tissue level and/or activity of at least one type of LOX or LOXL can modulate angiogenesis, primary tumor development, tumor metastasis and/or PAP. Expression level or activity of the LOX or LOXL can also be detected and used to diagnose a condition, such as PAP.

As used herein, the phrase "tissue level" refers to the level of LOX or LOXL protein present in the tissue at a given time point. At times, it may be advantageous to measure tissue levels of the active forms of LOX or LOXL. Protein levels are determined by factors such as, transcription and/or translation rates, RNA or protein turnover and/or protein localization within the cell. As such any molecule which effects any of these factors can modify the tissue level of LOX or LOXL.

As used herein the term "activity" refers to an enzymatic activity of LOX or LOXL. A molecule which can modify the enzymatic activity may directly or indirectly alter substrate specificity of the enzyme or activity of the catalytic site thereof.

There are numerous examples of compositions that can comprise molecules which can specifically modify the tissue level and/or activity of a lysyl oxidase. Such molecules can be categorized into lysyl oxidase "downregulators" or "upregulators."

Downregulators

One example of an agent capable of downregulating a lysyl oxidase protein is an antibody or antibody fragment capable of specifically binding lysyl oxidase or at least part of the lysyl oxidase protein (e.g., region spanning the catalytic site) and inhibiting its activity when introduced into the mammalian tissue. As such, an antibody or an antibody fragment directed at a lysyl oxidase can be used to suppress or arrest the formation of blood vessels, and to inhibit tumor fibrosis and metastasis.

The antibody can specifically bind to at least one epitope of LOX or LOXL. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three-dimensional structural characteristics, as well as specific charge characteristics.

As used herein, the term "antibody" includes intact molecules as well as functional fragments thereof, such as Fab, $F(ab')_2$, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) $(Fab')_2$, the fragment of the antibody that can be obtained by treating whole antibody with the enzyme pepsin without subsequent reduction; $F(ab')_2$ is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, *Antibodies: A Laboratory Manual*, Cold Spring Harbor Laboratory, New York 1988).

Antibody fragments according to the present disclosure can be prepared by proteolytic hydrolysis of the antibody or by expression in *E. coli* or mammalian cells (such as in Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5 S fragment denoted $F(ab')_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly. These methods are described, for example, by Porter, *Biochem. J.* 73:119-126 (1959), and U.S. Pat. Nos. 4,036,945 and 4,331,647, and references contained therein. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., *Proc. Nat. Acad. Sci.* USA 69: 2659-62 (1972). Alternatively, the variable chains can be linked by an intermolecular disulfide bond or cross-linked by chemicals such as gluteraldehyde. The Fv fragments can comprise VH and VL chains connected by a peptide linker. These single-chain antigen binding proteins (sFv) can be prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, *Methods* 2:97-105 (1991); Bird et al., *Science* 242:423-426 (1988); Pack et al., *Bio/Technology* 11:1271-77 (1993); and U.S. Pat. No. 4,946,778.

Another form of an antibody fragment is a peptide coding for a single complementarity-determining region (CDR).

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells, for example, as described in Larrick and Fry, *Methods*, 2:106-10 (1991).

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies), which contain minimal sequence derived from non-human immunoglobulin. Humanized antibodies include human immunoglobulins (recipient antibody) in which residues form a CDR of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally can also comprise at least a portion of an immunoglobulin constant region (Fe), typically that of a human immunoglobulin (Jones et al., *Nature*, 321:522-525 (1986); Riechmann et al., *Nature*, 332: 323-329 (1988); Presta, *Curr. Op. Struct. Biol.*, 2:593-596 (1992)).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., *Nature*, 321: 522-525 (1986); Riechmann et al., *Nature* 332: 323-327 (1988); Verhoeyen et al., *Science*, 239: 1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.*, 227:381-388 (1991); Marks et al., *J. Mol. Biol.*, 222:581-597 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985); Boerner et al., *J. Immunol.*, 147:86-95 (1991)). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10:779-783 (1992); Lonberg et al., *Nature* 368:856-859 (1994); Morrison, *Nature* 368:812-13 (1994); Fishwild et al., *Nature Biotechnology* 14:845-851 (1996); Neuberger, *Nature Biotechnology* 14:826 (1996); and Lonberg and Huszar, *Intern. Rev. Immunol.* 13:65-93 (1995).

As is described below, various approaches can be used to reduce or abolish transcription or translation of a lysyl oxidase.

Polynucleotides

One approach is the use of polynucleotides to downregulate the expression or activity of LOX or LOXL. "Polynucleotide," "nucleotide," "nucleic acid," and "oligonucleotide" are used interchangeably herein. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. An oligonucleotide may be isolated, such that the oligonucleotide is separated from other constituents, cellular and otherwise, that in nature is normally associated with the polynucleotide, peptide, polypeptide, protein, antibody, or fragments thereof.

Modified polynucleotides may be used in the present invention. Modified polynucleotides can have improved half-life and/or membrane penetration. A large number of variations in polynucleotide backbones are known in the arts. Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, anomeric bridges and borane derivatives, such as in Cook, *Anti-Cancer Drug Design* 6: 585 (1991).

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO2—).

International patent application WO 92/20702 describes an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group can be placed at the C-terminal region.

A linear sequence or sequence is an order of nucleotides in a polynucleotide in a 5' to 3' direction in which residues that neighbor each other in the sequence are contiguous in the primary structure of the polynucleotide. A partial sequence is a linear sequence of part of a polynucleotide that is known to comprise additional residues in one or both directions.

A linear sequence of nucleotides is identical to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotides, the sequence for the DNA reflects the order of nitrogenous bases in the polydeoxyribonucleotides, and the two sequences satisfy the other requirements of this definition. Where one or both of the polynucleotides being compared is double-stranded, the sequences are identical if one strand of the first polynucleotide is identical with one strand of the second polynucleotide.

A vector may comprise the polynucleotides of the present invention. The vector, a nucleic acid molecule that is typically self-replicating, transfers an inserted nucleic acid molecule into and/or between host cells. Vectors include those that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An expression vector is a polynucleotide which, when introduced into an appropriate host cell, can be transcribed and translated into a polypeptide(s). An expression system usually connotes a suitable host cell comprised of an expression vector that can function to yield a desired expression product.

Host cells into which a vector or polynucleotide of the invention, e.g., an expression vector, or an isolated nucleic acid molecule of the invention has been introduced, refers not only to the particular cell but also to the progeny or potential progeny of such a cell. A host cell can be any prokaryotic or eukaryotic cell. For example, host cells can include bacterial cells such as *E. coli*, insect cells, yeast cells, or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, calcium phosphate precipitation, electroporation, heat shock, lipofection, microinjection, and viral-mediated nucleic acid transfer. Delivery strategies are described in Luft, *J. Mol. Med.* 76:75-76 (1998); Kronenwett et al., *Blood* 91:852-862 (1998); Rajur et al., *Bioconjug. Chem.* 8:935-940 (1997); Lavigne et al., *Biochem. Biophys. Res. Commun.* 237:566-571 (1997) and Aoki et al., *Biochem. Biophys. Res. Commun.* 231:540-545 (1997). Delivery of the polynucleotides of the present invention can also be to subjects, including mammals. For example, polynucleotides of the present invention can be delivered or administered to mammalian tissues.

Polynucleotides of the present invention includes antisense oligonucleotides, ribozymes, DNAzymes, siRNA molecules including shRNA, and triple helix forming oligonucleotides, to downregulate the expression or activity of one or more lysyl oxidase.

Antisense Polynucleotides

According to one aspect, downregulation of LOX or LOXL levels or activity can be effected using an antisense polynucleotide capable of specifically hybridizing with an mRNA transcript encoding LOX or LOXL, such as LOXL2.

Design of antisense molecules which can be used to efficiently downregulate LOX or LOXL2 is typically effected while considering two aspects factors used in the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

Several considerations are typically taken into account when designing antisense oligonucleotides. For efficient in vivo inhibition of gene expression using antisense oligonucleotides or analogs, the oligonucleotides or analogs typically fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity. Algorithms for identifying those sequences with the highest predicted binding affinity for their target mRNA based on a thermodynamic cycle that accounts for the energy of structural alterations in both the target mRNA and the oligonucleotide are available, for example, as described in Walton et al. *Biotechnol Bioeng* 65:1-9 (1999).

Such algorithms have been successfully used to implement an antisense approach in cells. For example, the algorithm developed by Walton et al. enabled scientists to successfully design antisense oligonucleotides for rabbit β-globin (RBG) and mouse tumor necrosis factor-α (TNF α) transcripts. The same research group has also reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system are also published (Matveeva et al., *Nature Biotechnology* 16: 1374-1375 (1998)).

An antisense molecule which can be used with the present disclosure includes a polynucleotide or a polynucleotide analog of at least 10 bases, for example, between 10 and 15, between 15 and 20 bases, at least 17, at least 18, at least 19, at least 20, at least 22, at least 25, at least 30, or even at least 40 bases which is hybridizable in vivo, under physiological conditions, with a portion of a polynucleotide strand encoding a polypeptide at least 50% homologous to SEQ ID NO:1, 4, 5 or 7 or at least 75% homologous to an N-terminal portion thereof as determined using the BestFit software of the Wisconsin sequence analysis package, utilizing the Smith and Waterman algorithm, where gap creation penalty equals 8 and gap extension penalty equals 2.

The antisense oligonucleotides used by the present disclosure can be expressed from a nucleic acid construct administered into the tissue, in which case inducible promoters can be used such that antisense expression can be switched on and off, or alternatively such oligonucleotides can be chemically synthesized and administered directly into the tissue, as part of, for example, a pharmaceutical composition.

The ability of chemically synthesizing oligonucleotides and analogs thereof having a selected predetermined sequence offers means for downmodulating gene expression. Four types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligonucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Unmodified oligonucleotides are typically impractical for use as antisense sequences since they have short in vivo half-lives, during which they are degraded rapidly by nucleases. Furthermore, they are often difficult to prepare in more than milligram quantities. In addition, such oligonucleotides are usually poor cell membrane penetrants. Thus, oligonucleotide analogs are usually devised in a suitable manner.

For example, problems arising in connection with double-stranded DNA (dsDNA) recognition through triple helix formation have been diminished by a clever "switch back" chemical linking, whereby a sequence of polypurine on one strand is recognized, and by "switching back," a homopurine sequence on the other strand can be recognized. Also, good helix formation has been obtained by using artificial bases, thereby improving binding conditions with regard to ionic strength and pH.

RNA oligonucleotides may also be used for antisense inhibition as they form a stable RNA-RNA duplex with the target, suggesting efficient inhibition. However, due to their low stability, RNA oligonucleotides are typically expressed inside the cells using vectors designed for this purpose. This approach may be used when attempting to target an mRNA that encodes an abundant and long-lived protein.

Antisense therapeutics can be used to treat many life-threatening diseases with a number of advantages over traditional drugs. Traditional drugs typically intervene after a disease-causing protein is formed. Antisense therapeutics, however, can block mRNA transcription/translation and intervene before a protein is formed, and since antisense therapeutics target only one specific mRNA, they can be more effective with fewer side effects than current protein-inhibiting therapy.

Several clinical trials have demonstrated safety, feasibility and activity of antisense oligonucleotides. For example, antisense oligonucleotides suitable for the treatment of cancer have been successfully used (Holmund et al., *Curr. Opin. Mol. Ther.* 1:372-385 (1999)), while treatment of hematological malignancies via antisense oligonucleotides targeting c-myb gene, p53 and Bcl-2 had entered clinical trials and had been shown to be tolerated by patients (Gerwitz, *Curr. Opin. Mol. Ther.* 1: 297-306 (1999)).

More recently, antisense-mediated suppression of human heparanase gene expression has been reported to inhibit pleural dissemination of human cancer cells in a mouse model (Uno et al., *Cancer Res* 61:7855-60 (2001)).

The first antisense drug was recently approved by the FDA. The drug, Fomivirsen, was developed by Isis, and is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Ribozyme

Another agent capable of downregulating a lysyl oxidase is a ribozyme molecule capable of specifically cleaving an mRNA transcript encoding a LOX or LOXL. Ribozymes are being increasingly used for the sequence-specific inhibition of gene expression by the cleavage of mRNAs encoding proteins of interest (Welch et al., *Curr. Opin. Biotechnol.* 9:486-496 (1998)). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders (Welch et al., *Clin. Diagn. Virol.* 10:163-171 (1998)). Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Inc.).

DNAzyme

Another agent capable of downregulating a lysyl oxidase is a DNAzyme molecule capable of specifically cleaving an mRNA transcript or DNA sequence of LOX or LOXL. DNAzymes are single-stranded polynucleotides which are capable of cleaving both single and double stranded target sequences (Breaker and Joyce, *Chemistry and Biology,* 2:655-660 (1995); Santoro and Joyce, *Proc. Natl. Acad. Sci. USA,* 943:4262-4266 (1997)). A general model (the "10-23" model) for the DNAzyme has been proposed. "10-23"

DNAzymes have a catalytic domain of 15 deoxyribonucleotides, flanked by two substrate-recognition domains of seven to nine to deoxyribonucleotides each. This type of DNAzyme can effectively cleave its substrate RNA at purine: pyrimidine junctions (Santoro and Joyce, *Proc. Natl. Acad. Sci. USA*, 943:4262-4266 (1997); Khachigian, *Curr. Opin. Mol. Ther.* 4:119-121 (2002)).

Examples of construction and amplification of synthetic, engineered DNAzymes recognizing single and double-stranded target cleavage sites have been disclosed in U.S. Pat. No. 6,326,174. DNAzymes of similar design directed against the human Urokinase receptor were recently observed to inhibit Urokinase receptor expression, and successfully inhibit colon cancer cell metastasis in vivo (Itoh et al., 2002, Abstract 409, *Ann Meeting Am. Soc. Gen. Ther.* www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

siRNA

Another mechanism of down regulating a lysyl oxidase at the transcript level is RNA interference (RNAi), an approach which utilizes small interfering dsRNA (siRNA or small hairpin RNA, shRNA) molecules that are homologous to the target mRNA and lead to its degradation (Carthew, *Curr. Opin. Cell. Biol.* 13: 244-248 (2001)). For example, infection of diverse types of cancer cells with expression of a LOXL2 specific shRNA is effective in altering both their morphology and invasiveness (Example 1).

RNA interference is typically a two-step process. In the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs (Hutvagner and Zamore, *Curr. Opin. Genet. Dev.* 12: 225-232 (2002); Bernstein, *Nature* 409:363-366 (2001)).

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and typically cleaves the mRNA into approximately 12 nucleotide fragments from the 3' terminus of the siRNA (Hutvagner and Zamore, *Curr. Opin. Genet. Dev.* 12: 225-232 (2002); Hammond et al., *Nat. Rev. Gen.* 2:110-119 (2001); Sharp, *Genes. Dev.* 15:485-490 (2001)). Although the mechanism of cleavage is still to be elucidated, research indicates that each RISC contains a single siRNA and an RNase (Hutvagner and Zamore, *Curr. Opin. Genet. Dev.* 12: 225-232 (2002)).

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC (Hutvagner and Zamore, *Curr. Opin. Genet. Dev.* 12: 225-232 (2002); Hammond et al., *Nat. Rev. Gen.* 2:110-119 (2001); Sharp, *Genes. Dev.* 15:485-490 (2001)). RNAi is also described in Tuschl, *Chem. Biochem.* 2: 239-245 (2001); Cullen, *Nat. Immunol.* 3:597-599 (2002); and Brand, *Biochem. Biophys. Act.* 1575:15-25 (2002).

Synthesis of RNAi molecules suitable for use with the present disclosure can be effected as follows. First, the LOX or LOXL mRNA sequence is scanned downstream of the AUG start codon for AA dinucleotide sequences. Occurrence of each AA and the 3' adjacent 19 nucleotides is recorded as potential siRNA target sites. The siRNA target sites are selected from the open reading frame, as untranslated regions (UTRs) are richer in regulatory protein binding sites. UTR-binding proteins and/or translation initiation complexes may interfere with binding of the siRNA endonuclease complex (Tuschl, *Chem. Biochem.* 2: 239-245 (2001)). It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html). Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Selected sequences can include those with low G/C content as these have been shown to be more effective in mediating gene silencing as compared to those with G/C content higher than 55%. Several target sites can be selected along the length of the target gene for evaluation. For better evaluation of the selected siRNAs, a negative control is used in conjunction. Negative control siRNA can include the same nucleotide composition as the siRNAs but lack significant homology to the genome. Thus, a scrambled nucleotide sequence of the siRNA may be used, provided it does not display any significant homology to any other gene.

The siRNA molecules of the present disclosure can be transcribed from expression vectors which can facilitate stable expression of the siRNA transcripts once introduced into a host cell. These vectors are engineered to express shRNAs, which are processed in vivo into siRNA molecules capable of carrying out gene-specific silencing (Brummelkamp et al., *Science* 296:550-553 (2002); Paddison et al., *Genes Dev.* 16:948-958 (2002); Paul et al., *Nature Biotech.* 20: 505-508 (2002); Yu et al., *Proc. Natl. Acad. Sci. USA* 99:6047-6052 (2002)).

ShRNAs are single-stranded polynucleotides with a hairpin loop structure. The single-stranded polynucleotide has a loop segment linking the 3' end of one strand in the double-stranded region and the 5' end of the other strand in the double-stranded region. The double-stranded region is formed from a first sequence that is hybridizable to a target sequence, such as a polynucleotide encoding LOXL2, or a LOXL2 mRNA, and a second sequence that is complementary to the first sequence, thus the first and second sequence form a double stranded region to which the linking sequence connects the ends of to form the hairpin loop structure. The first sequence can be hybridizable to any portion of a polynucleotide encoding LOXL2. The double-stranded stem domain of the shRNA comprises a restriction endonuclease site.

The stem-loop structure of shRNAs can have optional nucleotide overhands, such as 2-bp overhangs, for example, 3' UU-overhangs. While there may be variation, stems typically range from approximately 15 to 49, approximately 15 to 35, approximately 19 to 35, approximately 21 to 31 bp, or approximately 21 to 29 bp, and the loops can range from approximately 4 to 30 bp, for example, about 4 to 23 bp.

For expression of shRNAs within cells, plasmid vectors containing either the polymerase III H1-RNA or U6 promoter, a cloning site for the stem-looped RNA insert, and a 4 5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

An example of a suitable expression vector is the pSUPER™, which includes the polymerase-III H1-RNA gene promoter with a well defined start of transcription and a termination signal consisting of five thymidines in a row (T5) (Brummelkamp et al., Science 296:550-553 (2002)). The cleavage of the transcript at the termination site is at a site following the second uridine, thus yielding a transcript which resembles the ends of synthetic siRNAs, which also contain nucleotide overhangs. siRNA is cloned such that it includes the sequence of interest, i.e., LOX or LOXL separated by a short spacer from the reverse complement of the same sequence. The resulting transcript folds back on itself to form a stem-loop structure, which mediates LOX or LOXL RNAi. For example, sequences that comprise a DNA sequence encoding the shRNA for LOXL2, such as SEQ ID NO: 20 (sh.LOXL2.197 or si-197), or SEQ ID NO: 21 (sh.LOXL2.195, or si-195) may medidate LOXL2 RNAi. The sequences that mediate LOXL2 RNAi may also comprise SEQ ID NO: 22, 23, 24, 25, 26, or portions thereof.

Another suitable siRNA expression vector encodes the sense and antisense siRNA under the regulation of separate polIII promoters (Miyagishi and Taira, Nature Biotech. 20:497-500 (2002)). The siRNA, generated by this vector also includes a five thymidine (T5) termination signal.

Since approaches for introducing synthetic siRNA into cells by lipofection can result in low transfection efficiencies in some cell types and/or short-term persistence of silencing effects, vector mediated methods have been developed.

Thus, siRNA molecules utilized by the present disclosure can be delivered into cell using retroviruses. Delivery of siRNA using retroviruses provides several advantages over methods, such as lipofection, since retroviral delivery typically is more efficient, uniform and immediately selects for stable "knock-down" cells (Devroe and Silver, BMC Biotechnol. 2:15 (2002)).

Recent scientific publications have validated the efficacy of such short double stranded RNA molecules in inhibiting target mRNA expression and thus have clearly demonstrated the therapeutic potential of such molecules. For example, RNAi has been utilized to inhibit expression of hepatitis C (McCaffrey et al., Nature 418:38-39 (2002)), HIV-1 (Jacque et al., Nature 418:435-438 (2002)), cervical cancer cells (Jiang and Milner, Oncogene 21:6041-6048 (2002)) and leukemic cells (Wilda et al., Oncogene 21, 5716-5724 (2002)).

Triple Helix Forming Oligonucleotides (TFO)

An additional method of regulating the expression of LOX or LOXL in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III et al., Science 245:725-730 (1989); Moser et al., Science 238:645-630 (1987); Beal et al., Science 251: 1360-1363 (1992); Cooney et al., Science 241:456-459 (1988); and Hogan et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (see Seidman and Glazer, J. Clin. Invest. 112:487-494 (2003)).

In general, the triplex-forming oligonucleotide has the sequence correspondence:

| oligo  | 3'--A | G | G | T |
|--------|-------|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors demonstrated that TFOs designed according to the A-AT and G-GC rule do not form non-specific triplexes, indicating that the triplex formation is sequence specific.

Thus for any given sequence in the LOX or LOXL regulatory region, a triplex forming sequence may be devised. Triplex-forming oligonucleotides can be at least 15, 25, 30 or more nucleotides in length. They can also be up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 27:1176-1181 (1999); Puri et al., J. Biol. Chem. 276: 28991-28998 (2001)), and the sequence and target specific downregulation of expression of the Ets2 transcription factor, important in prostate cancer etiology (Carbone et al., Nucl. Acid Res. 31:833-843 (2003)), and the pro-inflammatory ICAM-1 gene (Besch et al., J. Biol. Chem. 277:32473-32479 (2002)). In addition, Vuyisich and Beal have shown that sequence specific TFOs can bind to dsRNA, inhibiting activity of dsRNA-dependent enzymes such as RNA-dependent kinases (Vuyisich and Beal, Nuc. Acids Res. 28: 2369-2374 (2000)).

Additionally, TFOs designed according to the abovementioned principles can induce directed mutagenesis capable of effecting DNA repair, thus providing both downregulation and upregulation of expression of endogenous genes (Seidman and Glazer, J. Clin. Invest. 112:487-494 (2003)). Detailed description of the design, synthesis and administration of effective TFOs can be found in U.S. Patent Application Nos. 2003/017068 and 2003/0096980 to Froehler et al, and 2002 0128218 and 2002 0123476 to Emanuele et al, and U.S. Pat. No. 5,721,138 to Lawn.

The downregulators described hereinabove are useful for inhibiting angiogenesis in tumor tissue. It has been shown that PF4, a lysyl oxidase binding protein which inhibits angiogenesis in tumor tissue specifically accumulates in newly formed blood vessels of tumors (angiogenic vessels) but not in established blood vessels (Hansell et al., Amer. J. Physiol-Heart. Circ. Phy. 38:H829-H836 (1995); Reiser et al., FASEB J. 6: 2439-2449 (1992)).

Newly formed angiogenic blood vessels are typically more permeable to proteins than established blood vessels because the major inducer of angiogenesis in many angiogenic diseases is VEGF, a growth factor which also functions as a potent blood vessel permeabilizing factor (VPF) (Neufeld et al., *FASEB J.* 13:9-22 (1999)). Tumor associated blood vessels are therefore typically in a permanent state of hyperpermeability due to deregulated over-expression of VEGF and as such, a downregulator molecule used by the method of the present disclosure could be able to extravasate efficiently from tumor blood vessels but much less efficiently from normal stabilized blood vessels.

Upregulators

Several approaches can be utilized to increase the levels of LOX or LOXL and as such to enhance the formation of blood vessels.

For example, a nucleic acid construct including a constitutive, inducible or tissue specific promoter positioned upstream of a polynucleotide encoding a polypeptide having LOX or LOXL activity, such as the polypeptide set forth in SEQ ID NO: 2, 3, 6, 8 or 9 can be administered into a mammalian tissue. The LOX or LOXL expressed from this construct could substantially increase the levels of LOX or LOXL within the cells of the tissue and as such enhance angiogenesis.

The polynucleotide segments encoding the LOX or LOXL can be ligated into a commercially available expression vector. Such an expression vector includes a promoter sequence for directing transcription of the polynucleotide sequence in the cell in a constitutive or inducible manner. A suitable promoter can be, for example, a Tie-2 promoter which is capable of directing lysyl oxidase specific gene expression in endothelial cells (see Schlaeger et al., *Proc. Natl. Acad. Sci. U.S.A.* 94, 3058-3063 (1997)). The expression vector of the present disclosure can further include additional polynucleotide sequences such as for example, sequences encoding selection markers or reporter polypeptides, sequences encoding origin of replication in bacteria, sequences that allow for translation of several proteins from a single mRNA such as an internal ribosome entry site (IRES), sequences for genomic integration of the promoter-chimeric polypeptide encoding region and/or sequences generally included in mammalian expression vector such as pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Strategene, pTRES which is available from Clontech, and their derivatives.

It will be appreciated that such commercially available vector systems can easily be modified via commonly used recombinant techniques in order to replace, duplicate or mutate existing promoter or enhancer sequences and/or introduce any additional polynucleotide sequences.

An agent capable of upregulating a LOX or LOXL may also be any compound which is capable of increasing the transcription and/or translation of an endogenous DNA or mRNA encoding a LOX or LOXL using for example gene "knock in" techniques.

Enhancer elements can be "knocked in" adjacent to endogenous lysyl oxidase coding sequences to thereby increase transcription therefrom.

Further details relating to the construction and use of knock-out and knock-in constructs is provided elsewhere (Fukushige and Ikeda, DNA Res. 3:73-80 (1996); Bedell et al., Genes Dev. 11:1-11 (1997); Bermingham et al., Genes Dev. 10:1751-1762 (1996)).

It will be appreciated that direct administration of a polypeptide exhibiting a LOX or LOXL activity can also be utilized for enhancing angiogenesis.

Thus, affinity binding assays and/or activity assays, the principles of which are well known in the art, can be used to screen for novel compounds (e.g., substrate analogs) which can specifically regulate the activity of a lysyl oxidase and as such can be used with the present invention.

An assay suitable for use with this aspect of the present disclosure has been previously described in a study conducted by Bedell-Hogan et al., *J Biol Chem.* 268:10345-10350 (1993).

Administration

Previous studies correlated expression levels of LOXL2 to the metastatic properties of breast cancer derived cell lines, indicating that LOXL2 may play additional roles in tumor invasiveness in addition to its role in angiogenesis.

Thus, the present disclosure provides a method of inhibiting metastasis and/or fibrosis in a mammalian tissue using compositions described herein. The method is effected by administering to the mammalian tissue a molecule capable of downregulating a tissue level and/or an activity of at least one type of a lysyl oxidase, such as shRNA disclosed herein.

The method of the present disclosure can be used to treat human patients that have been diagnosed with cancerous tumors, by administering any of the downregulating molecules described herein above, in order to reduce the tissue level and/or activity of at least one type of a lysyl oxidase.

As used herein, the phrase "cancerous tumor" refers to any malignant tumor within a human body including, but not limiting to, tumors with metastases. In addition, and without being bound to any particular type of cancerous tumor, the present disclosure is useful to treat breast cancer tumors, with or without metastases.

As used herein, the phrase "administering" refers to all modes of administration described herein below with respect to the pharmaceutical compositions of the present invention. Administration also refers to all modes of administration described herein below with respect to any agent, including polynucleotides of the present invention, for a therapeutic effect. Administration may be of an amount effective to have a therapeutic effect. The therapeutic effect may be for treating or inhibiting a condition or disorder, such as cancerous tumors, primary or metastatic, PAP, as well as disorders or conditions associated with fibrosis, and/or angiogenesis. An effective amount as used herein refers the amount or dosage of that composition, such as an agent, including polynucleotides of the present invention that is required to induce a desired effect. An effective amount amount of a pharmaceutical composition, or of an agent, such as a polynucleotide is meant to be a nontoxic but sufficient amount of the agent or composition, to provide the desired effect, i.e., inhibiting, preventing, or reversing, the onset or progressive course of a cancer, primary or metastatic, PAP, inflammation, and/or conditions or disorders related to fibrosis or angiogenesis.

Administration includes, but is not limited to, local administration at the tumor tissue, an organ where the cancerous tumor was diagnosed and/or related tissues that typically form metastases (Hortobagyi, *Semin. Oncol.* 29: 134-144 (2002); Morrow and Gradishar, *BMJ* 324:410-414 (2002)). Examples of related tissue include lymph nodes adjacent to, for example, breast tissue and bones.

Administration can also be effected in a systemic manner in order to treat the affected tissue, i.e., the tissue where the cancerous tumor was formed and where metastases are present or likely to be formed with tumor progression. A therapeutically effective amount of compositions described herein, may be administered, in which the amount is nontoxic but sufficient to provide the desired effect, i.e., inhibiting, preventing, or reversing the onset or progressive course of a condition described here, including primary tumor formation or growth, metastasis, fibrosis, angiogenesis, and PAP.

Since any molecule capable of downregulating a lysyl oxidase activity can be utilized by the methods described hereinabove, the present disclosure also provides a method of identifying molecules capable of inhibiting metastasis and/or fibrosis.

This method is effected by screening and identifying molecules which exhibit specific reactivity with at least one type of lysyl oxidase and testing a metastasis and/or fibrosis inhibitory potential of these molecules.

Numerous types of molecules can be screened for reactivity with at least one type of lysyl oxidase, examples include, but are not limited to, molecules such as antisense oligonucleotides, siRNA, DNAzymes, ribozymes and triple helix forming oligonucleotides (TFOs) that interact with a polynucleotide expressing a lysyl oxidase activity or molecules such as antibodies that interact with polypeptides having a lysyl oxidase activity. In addition, short peptides and other small molecules can also be screened by this method and used in the compositions and methods of treatments disclosed herein.

Screening for cross reactivity can be effected by lysyl oxidase enzymatic activity assays, by binding assays and the like. Examples of suitable assays are provided in Rodriguez et al., *Arterioscler. Thromb. Vasc. Biol.* 22:1409-1414 (2002); Wilson and Nock, *Curr. Opin. Chem. Biol.* 6:81-85 (2002); Uetz, *Curr. Opin. Chem. Biol.* 6: 57-62 (2002); Stoll et al., *Front Biosci.* 7:c13-32 (2002)).

Testing a metastatic phenotype of transformed tumor cells can be performed in vitro since nearly all steps of the metastatic process, including attachment, matrix degradation and migration, can be modeled experimentally in vitro by measuring invasion of a reconstituted basement membrane (RBM). Metastatic invasiveness of tumor cell can be modeled by migration of tumor cells into reconstituted basement membrane (RBM) in the presence and absence of a chemoattractant, such as fibroblast conditioned medium (FCM). The assay determines cells that have attached to the RBM, degraded the RBM enzymatically and, finally, cells that have penetrated the FCM side of the membrane.

Since in vitro metastasis events correspond to steps observed in the metastatic spread of tumor cells through the basement membrane in vivo, in vitro invasiveness of cells can be assayed by the methods described in Albini et al., *Cancer Res.* 47:3239-3245 (1987). Invasiveness assays and other methods for assessing metastatic affects, are described in Leyton et al., *Cancer Res.* 54:3696-3699 (1994). Reconstituted basement membrane preparations for use in accordance with the hereinabove described assays are readily available from numerous commercial suppliers. One such example membrane in this regard is "MATRIGEL" available from Collaborative Biomedical Products of Bedford, Mass.

In vitro evaluation of tumor cell metastatic phenotype can also be effected by determining level and pattern of expression of one or more metastasis associated markers such protease markers, which are considered to be an integral part of tumor metastasis (see U.S. Pat. No. 6,303,318). One example is the arachidonic acid, the release of which in cells can serve to indicate metastatic potential of a tumor (U.S. Pat. No. 6,316,416). In this regard, determining phospholipase A-2 (PLA2) activity, and the activity or abundance of factors that affect the activity of PLA2, such as uteroglobin protein (U.S. Pat. No. 6,316,416) can serve as an indication of metastatic potential.

Determining pattern and level of expression of metastasis-associated markers can be effected by one of several methods known in the art.

The presence or level of proteins indicative of metastatic potential of tumors can be determined in cells by conventional methods well known to those of skill in the art. For instance, the techniques for making and using antibody and other immunological reagents and for detecting particular proteins in samples using such reagents are described in Coligan et al. (Eds.), *Current Protocols in Immunology*, John Wiley & Sons, New York (1995), which is incorporated by reference herein in parts pertinent to making and using reagents useful for determining specific proteins in samples. As another example, immunohistochemical methods for determining proteins in cells in tissues are described in Ausubel et al., (Eds.), *Current Protocols in Molecular Biology*, Volume 2, Chapter 14, John Wiley & Sons, Inc. (1994), which is incorporated by reference herein in part pertinent to carrying out such determinations. Finally, Linnoila et al., *A.J.C.P.* 97: 235-243 (1992) and Peri et al., *J. Clin. Invest.* 92: 2099-2109 (1992), incorporated herein as referred to above, describe techniques that may be used.

Metastatic potential can also be determined in vivo at the mRNA level. The presence and/or level of mRNA transcripts can be determined by a variety of methods known to those of skill in the art. A given mRNA may be detected in cells by hybridization to a specific probe. Such probes may be cloned DNAs or fragments thereof, RNA, typically made by in vitro transcription, or oligonucleotide probes, usually generated by solid phase synthesis. Methods for generating and using probes suitable for specific hybridization are well known and used in the art.

A variety of controls may be usefully employed to improve accuracy in mRNA detection assays. For instance, samples may be hybridized to an irrelevant probe and treated with RNAse A prior to hybridization, to assess false hybridization.

In order to modulate angiogenesis or inhibit metastasis or tumor fibrosis, the molecules used by the present disclosure can be administered to the individual per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration/targeting of a compound to a mammal.

As used herein the term "active ingredients" refers to the preparation accountable for the biological effect, i.e. the upregulator/downregulator molecules used by the present disclosure to modulate angiogenesis and the downregulators molecules used by the present disclosure to inhibit metastasis and tumor fibrosis.

The phrases "physiologically acceptable carrier" and "pharmaceutically acceptable carrier" are interchangeably used to refer to a carrier, such as, for example, a liposome, a virus, a micelle, or a protein, or a diluent which do not cause significant irritation to the mammal and do not abrogate the biological activity and properties of the active ingredient. An adjuvant is included under these phrases.

The term "excipient" refers to an inert substance added to a pharmaceutical composition to further facilitate administration of an active ingredient. Examples, without limitation, of excipients, include calcium carbonate, calcium phosphate, various sugars and types of starch, cellulose derivatives, gelatin, vegetable oils and polyethylene glycols.

Techniques for formulation and administration of compositions may be found in *Remington's Pharmaceutical Sciences*, Mack Publishing Co., Easton, Pa., latest edition.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active ingredient with pharmaceutically acceptable carriers well known in the art. Such carriers enable the active ingredient of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present disclosure may also be formulated in rectal compositions such as suppositories or retention enemas, using, e.g., conventional suppository bases such as cocoa butter or other glycerides.

Pharmaceutical compositions suitable for use in context of the present disclosure include compositions wherein the active ingredients are contained in an amount effective to achieve the intended purpose.

The pharmaceutical composition may form a part of an article of manufacturing which also includes a packaging material for containing the pharmaceutical composition and a leaflet which provides indications of use for the pharmaceutical composition.

Thus, the present disclosure provides methods and pharmaceutical compositions useful modulating angiogenesis.

Such modulation activity can be used to treat arthritis (Koch, *Arthritis Rheum.* 41:951-962 (1998); Paleolog and Fava, Springer *Semin. Immunopathol.* 20: 73-94 (1998)), diabetic retinopathy (Miller et al., *Diabetes Metab. Rev.* 13:37-50 (1997)), psoriasis, (Detmar et al., *J. Exp. Med.* 180:1141-1146 (1994); Creamer et al., *Br. J. Dermatol.* 136, 859-865 (1997)) or vasculitis (Lie, *Curr. Opin. Rheumatol.* 4:47-55 (1992); Klipple and Riordan, *Rheum. Dis. Clin.* North Am. 15:383-398 (1989)).

In addition, the present disclosure also provides methods to treat disease characterized by fragile blood vessels, including Marfans syndrome, Kawasaki, Ehlers-Danlos, cutis-laxa, and takysu (Lie, *Curr. Opin. Rheumatol.* 4:47-55 (1992); Klipple and Riordan, *Rheum. Dis. Clin.* North Am. 15:383-398 (1989); Brahn et al., *Clin. Immunol. Immunopathol.* 90:147-151 (1999); Cid et al., *J. Clin. Invest.* 91:977-985 (1993); Hoffman et al., *Arthritis Rheum.* 34:1466-1475 (1991)). It is possible that some of these diseases result from reduced or abolished lysyl oxidase activity which leads to the synthesis of a fragile extracellular matrix, and consequently, fragile blood vessels. As such, administration of LOX or LOXL encoding sequences or polypeptides can be used to correct some of the manifestations of these diseases.

The present disclosure also provides methods to treat diseases which are characterized by changes in the wall of blood vessels. For example, restenosis which is a common complication following balloon therapy, fibromuscular dysplasia (Begelman and Olin, *Curr. Opin. Rheumatol.* 12:41-47 (2000)) and aortic stenosis (Palta et al., *Circulation* 101: 2497-2502 (2000)) are all potentially treatable by the compositions and methods described herein.

Diagnostics

In addition, LOXL2 is more highly expressed in metastatic tumors and cell lines than in non-metastatic tumors and cell lines. This suggests that levels of LOXL2 expression can be used as a diagnostic tool to determine the malignancy of cancer cells, as well as, to determine and implement suitable treatment regimens. LOXL2 and LOXL3 are also more highly expressed in PAP, and thus levels to of LOXL2, LOXL3, or both, can be used as a diagnostic tool to determine PAP and implement suitable treatment regimens. Detection agents, such as an antibody, a small molecule, antisense molecule, ribozyme, DNAzyme, triple helix forming oligonucleotides, siRNA, or shRNA can be used to assess the level or activity of LOXL2, LOXL3, or both, in subjects.

Colon cancer is a highly treatable and often a curable disease when localized to the bowel. However, in many cases, due to mis-diagnosis, a pre-malignant colon hyperplasia progress into colon adenoma which further develop into more malignant forms of low-grade and high-grade colon adenocarcinoma. Once an individual is diagnosed with colon cancer the malignancy of the tumor needs to be assessed in order to select for suitable treatment regimens. The current practice for assessing the malignancy of a colon tumor is based on the tumor-node-metastases (TNM) staging system developed by the American Joint Committee on Cancer (AJCC). According to this method staging is based on scoring for the presence or absence of cancerous cells in the tumor itself, in the submucosa of the bowel wall, in the muscular layer of the bowel wall (muscularis propria), and/or in the subserosa, pericolic or perirectal tissues, as well as in regional lymph nodes and distance metastases. Thus, staging of colon tumors involves multiple tissue biopsies and complex pathological evaluations which are time consuming and can result in misdiagnosis.

LOXL2 expression in epithelial and/or connective tissue cells in a colon tissue is indicative of a malignant colon cancer and thus provides a new method of assessing a malignancy of colon cancer tumors devoid of the above limitations.

The expression of LOXL2 is correlated with the formation of benign colon tumors and is increased in more malignant forms of colon cancer tumors thus suggesting the use of LOXL2 in determining the stage of colon cancer tumors.

Thus according to another aspect of the present disclosure there is provided a method of assessing a malignancy of a colon tumor. The method is effected by determining a tissue level and/or an activity level of a polypeptide at least 75% homologous to the polypeptide set forth in SEQ ID NO: 2 or 9 in the colon tumor tissue, thereby assessing the malignancy of the colon tumor.

As is used herein, the phrase "assessing a malignancy of a colon tumor" refers to determining the stage of the colon tumor, i.e., the progress of the colon tumor from a benign colon tumor to a highly malignant colon cancer which invades the surrounding tissue.

The polypeptide detected by the present disclosure can be at least 75%, at least 80%, at least 85%, at least 90%, or at least 95% homologous to SEQ ID NO: 2 or 9, as determined using the BestFit software of the Wisconsin sequence analysis package, utilizing the Smith and Waterman algorithm, where gap creation penalty equals 8 and gap extension penalty equals 2.

In some embodiments, the polypeptide is LOXL2 (SEQ ID NO: 2), a member of the lysyl oxidase family which are fully described herein.

According to the methods described herein, a colon tumor tissue is obtained using a colon biopsy and/or a colon surgery using methods know in the art. Once obtained, the tissue level and/or activity level of the polypeptide of the present disclosure is determined in the colon tumor tissue.

Similarly, for PAP diagnosis, a lung tissue sample can be obtained by lung biopsy and other methods known in the art.

The polypeptide detected by the present disclosure can be at least 75%, at least 80%, at least 85%, at least 90%, or at least 95% homologous to SEQ ID NO: 2 or 9, as determined using the BestFit software of the Wisconsin sequence analysis package, utilizing the Smith and Waterman algorithm, where gap creation penalty equals 8 and gap extension penalty equals 2. The polypeptide of the present disclosure can be LOXL2 (SEQ ID NO: 2) or LOXL3 (SEQ ID NO. 9), members of the lysyl oxidase family which are fully described herein. The mRNA expression can also be detected and used for diagnosis. Furthermore, both LOXL2 and LOXL3 can be detected, either using the same detection agent (for example an antibody that detects both proteins), or different detection agents (for example an antibody that is specific for LOXL2 and another antibody specific for LOXL3; or different Northern probes).

Determination of the tissue level of the polypeptides described herein may be accomplished directly using immunological methods.

The immunological detection methods used in context of the present disclosure are fully explained in, for example, Lane (Ed.), *Using Antibodies: A Laboratory Manual*, Ed Harlow, Cold Spring Harbor Laboratory Press (1999) and those familiar with the art will be capable of implementing the various techniques summarized hereinbelow as part of the present invention. All of the immunological techniques require antibodies specific to at least one epitope of the polypeptide of the present invention. Immunological detection methods suited for use as part of the present disclosure include, but are not limited to, radio-immunoassay (RIA), enzyme linked immunosorbent assay (ELISA), western blot, immunohistochemical analysis.

Radio-Immunoassay (RIA):

In one version, this method involves precipitation of the desired substrate, e.g., LOXL2, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme Linked Immunosorbent Assay (ELISA):

This method involves fixation of a sample (e.g., fixed cells or a proteinaceous solution) containing a protein substrate (e.g., LOXL2) to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot Analysis:

This method involves separation of a substrate (e.g., LOXL2) from other proteins by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical Analysis:

This method involves detection of a substrate in situ in fixed tissue by substrate specific antibodies. The substrate specific antibodies may be enzyme linked or linked to fluorophores and detected by microscopy and subjective evaluation. If enzyme linked antibodies are employed, a colorimetric reaction may be employed.

Since tissue levels of a polypeptide can be inferred from the levels of mRNA encoding such a polypeptide, the method according to this aspect of the present disclosure can also employ various polynucleotide detection approaches for determining the tissue level of the polypeptide of the present invention.

RNA molecules can be detected using methods known in the art including for example, Northern blot analysis, RT-PCR analyses, RNA in situ hybridization stain and in situ RT-PCR stain.

Northern Blot Analysis:

This method involves the detection of a particular RNA (e.g., the RNA molecule encoding LOXL2) in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence as described hereinabove. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules from a particular tissue (e.g., a colon tumor tissue) are purified and converted into complementary DNA (cDNA) using a reverse transcriptase enzyme (such as an MMLV-RT) and primers such as, oligo dT, random hexamers or gene specific primers, all of which are available from Invitrogen Life Technologies, Frederick, Md., USA. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules.

RNA In Situ Hybridization Stain:

In this method DNA or RNA probes are attached to the RNA molecules present in the tissue. Generally, a tissue sample (e.g., a colon tissue) is fixed to preserve its structure and to prevent the RNA from being degraded and then sectioned for microscopy and placed on a slide. Alternatively, frozen tissue samples can be first sectioned and put on a slide and then subject to fixation prior to hybridization. Hybridization conditions include reagents such as formamide and salts (e.g., sodium chloride and sodium citrate) which enable specific hybridization of the DNA or RNA probes with their target mRNA molecules in situ while avoiding non-specific binding of probe. Those of skill in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes as described hereinabove.

In Situ RT-PCR Stain:

This method is described in Nuovo et al., *Am. J. Surg. Pathol.* 17:683-690 (1993) and Komminoth et al., *Pathol. Res. Pract.* 190:1017-1025 (1994). Briefly, the RT-PCR reaction is performed on fixed tissue sections by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Determination of an activity level of the polypeptide of the present disclosure (e.g., LOXL2) in a colon tumor tissue may be effected using suitable substrates in a cytochemical stain and/or in vitro activity assays.

Cytochemical Stain:

According to this method, a chromogenic substrate is applied on the colon tumor tissue containing an active enzyme (e.g., LOXL2). The enzyme catalyzes a reaction in which the substrate is decomposed to produce a chromogenic product visible by a light or a fluorescent microscope.

In Vitro Activity Assays:

In these methods the activity of a particular enzyme is measured in a protein mixture extracted from the tissue of interest (e.g., a colon tumor tissue). The activity can be measured in a spectrophotometer well using colorimetric methods (see for example, Wande et al., *Proc. Natl. Acad. Sci. USA*. 1997, 94: 12817-12822 (1997)) or can be measured in a non-denaturing acrylamide gel (i.e., activity gel). Following electrophoresis the gel is soaked in a solution containing a substrate and colorimetric reagents. The resulting stained band corresponds to the enzymatic activity of the polypeptide of interest (e.g., LOXL2). If well calibrated and within the linear range of response, the amount of enzyme present in the sample is proportional to the amount of color produced. An enzyme standard is generally employed to improve quantitative accuracy.

Once the tissue level and/or the activity level of the polypeptide (or mRNA) of the present disclosure (e.g., LOXL2) is determined in the colon tumor tissue the malignancy of the tumor is assessed by comparing the expression level and/or activity in the colon tumor tissue to that of a normal colon tissue.

It will be appreciated that the normal colon tissue may be obtained from a biopsy and/or a surgery of a colon tissue obtained form a healthy individual. Alternatively, the normal colon tissue can be obtained from an unaffected segment of the colon of the same individual. Methods of determining the status of a normal colon tissue are known to skilled in the art and include for example, a morphological evaluation of tissue sections.

Once malignancy of colon cancer is determined as described above, tissue level and/or activity level of the polypeptide (or mRNA thereof) of the present disclosure can also be utilized to stage the colon tumor and to thereby predict the prognosis of an individual diagnosed with colon cancer.

Such staging can be effected by assessing the tissue level and/or activity level of the polypeptide and correlating it to results obtained from colon cancer tissue at various stages (obtainable through pathological evaluation of colon tumors). It will be appreciated that such accurate and rapid staging will enable accurate and rapid prognosis of an individual afflicted with colon cancer and timely administration of suitable treatment regimen.

Additional objects, advantages, and novel features of the present disclosure will become apparent to one of skill in the art. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. Additionally, each of the various embodiments and aspects of the present disclosure as delineated hereinabove and as claimed in the claims section below finds experimental support in the following examples.

EXAMPLES

Generally, the nomenclature used herein and the laboratory procedures utilized in the present disclosure include molecular, biochemical, microbiological and recombinant DNA techniques. Such techniques are thoroughly explained in the literature. See, for example, Sambrook et al., *Molecular Cloning: A Laboratory Manual*, (1989); Ausubel (Ed.), *Current Protocols in Molecular Biology*, Volumes I-III, John Wiley and Sons, Baltimore, Md. (1994); Perbal, *A Practical Guide to Molecular Cloning*, John Wiley & Sons, New York (1988); Watson et al., *Recombinant DNA*, Scientific American Books, New York; Birren et al. (Eds.), *Genome Analysis: A Laboratory Manual Series*, Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; Cellis (Ed), *Cell Biology: A Laboratory Handbook*, Volumes I-III, (1994); Coligan (Ed), *Current Protocols in Immunology*, Volumes I-III (1994); Stites et al. (Eds.), *Basic and Clinical Immunology* (8th Edition), Appleton & Lange, Norwalk, Conn. (1994); Mishell and Shiigi (Eds.), *Selected Methods in Cellular Immunology*, W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; Gait (Ed), *Oligonucleotide Synthesis*, (1984); Hames and Higgins (Eds.), *Nucleic Acid Hybridization*, (1985); Hames and Higgins (Eds.), *Transcription and Translation*, (1984); Freshney (Ed.), *Animal Cell Culture*, (1986); *Immobilized Cells and Enzymes*, IRL Press (1986); and *Methods in Enzymology*, Vol. 1-317, Academic Press; *PCR Protocols: A Guide To Methods And Applications*, Academic Press, San Diego, Calif. (1990); Marshak et al., *Strategies for Protein Purification and Characterization—A Laboratory Course Manual*, CSHL Press (1996).

Example 1

ShRNA Against LOXL2 Inhibits Tumor Cell Invasiveness

Materials and Methods

Lentiviral expression plasmids containing several candidate DNA sequences encoding candidate shRNA species directed against LOXL2 and a DNA encoding a gene that confers resistance to the selective agent puromycin were bought by us from Sigma (St. Louis, Mich.) (FIG. 1). Lentiviruses containing these candidate cDNAs were produced in the HEK293-T packaging cell line by transfection of the plasmids into the cells along with the packaging vector pCM-VdR8.91, and a plasmid encoding the vesicular stomatitis virus coat envelope pMD2-VSVG (5 µg). Recombinant replication defective lentiviruses were collected from the conditioned medium of the packaging cells and used to infect target tumor cells. The tumor invasion assay is illustrated in FIG. 2. Tumor cells are seeded between two layers of collagen in a monolayer, which represents the tumor mass. The cells invade over time the adjacent layers of collagen. The number of invading cells to various depths in microscopic fields is counted automatically using the Image-Pro morphometric analysis software.

Results

The different lentiviruses carrying the different candidate DNA species encoding the different shRNAs were screened for their ability to inhibit the expression of LOXL2. None of these cDNA species has any homology to the sequences of other members of the lysyl-oxidase family of genes. Two of these cDNA species were found to encode shRNA species that inhibit the expression of LOXL2 at the mRNA and protein level. The DNA sequence encoding the first shRNA is GAAGGAGACATCCAGAAGAAT (sh.LOXL2.197 or si-197; SEQ ID NO: 20) and the second has the sequence CGATTACTCCAACAACATCAT (sh.LOXL2.195, or si-195; SEQ ID NO: 21). Of these two, si-195 is believed to be a slightly more potent inhibitor (FIG. 3A).

The invasive/metastatic phenotype is associated in many instances with a transition from an epithelial to a mesenchymal morphology (EMT). Expression of the shRNA species in the human derived tumorigenic cell lines induced a dramatic shift in morphology from a mesenchymal to an epithelial morphology (FIG. 4).

Figure 5C:
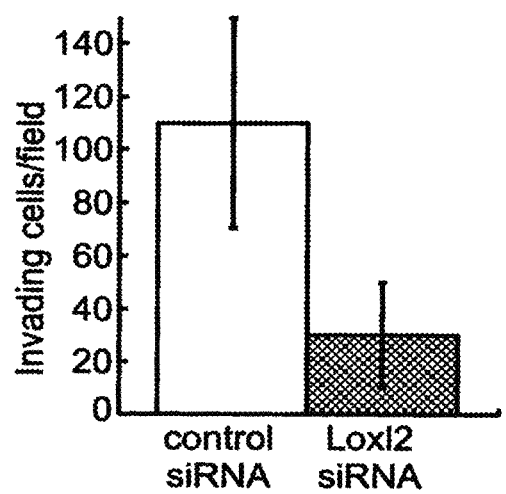

In order to assess the effects of the shRNA species on the invasiveness of the cells, tumor cells indected with control lentiviruses or tumor cells infected with the lentiviruses encoding the si-195 shRNA were seeded between two layers of collagen and their ability to invade the collagen above and below the monolayer of cells assessed. It can be seen that expression of the si-195 shRNA substantially inhibited the invasiveness of the cells into the collagen layers above and below the original monolayer of cells (FIG. 5).

Example 2

LOXL2 is Overexpressed in Primary Alveolar Proteinosis

Primary alveolar proteinosis (PAP) is characterized by over-secretion of lung surfactant, and is a problematic condition of unknown etiology, which presents difficulties for both diagnosis and effective treatment.

Expression of LOXL2 and LOXL3 was assessed in lungs of normal and PAP patients. FIG. 6 shows overexpression of LOXL2 in pulmonary endothelial cells in PAP, while LOXL3 is expressed in the smooth muscle.

Example 3

LOXL2 shRNA Promotes MET in Malignant Human Cells

LOXL2-induced EMT in three types of malignant human cells, 10HT1080, MDA-MB-231, or Yu/PAC2 cells. $2\times10^5$ cells, were seeded in 35 mm dishes. The cells were infected with lentivirus directing expression of LOXL2 shRNA, shR-NA.Loxl2.195 or control shRNA (FIG. 7) according to the vendor protocol (Sigma). Phalloidin staining of cells was performed by fixing cells in 4% paraformaldehyde. The cells were then permeabilised with 0.05% saponin before being stained with rhodamine-phalloidin (Molecular Probes, Eugene, Oreg.) (FIG. 7). Cells treated with shR-NA.Loxl2.195 appeared to be in mesenchymal-epithelial transition (MET) states.

Calcium Phosphate Transfections:

Calcium phosphate transfections were performed for retroviral production. Generally, the plates were pre-coated with 0.2% sterilized Gelatin to ensure better adherence of the cells during all phases of the protocol. For 100 mm plate ~2.5-3.0× $10^6$ cells were seeded for 293, 293T cells and 3.2-3.5×$10^6$ cells for ΦNX-A cells 18-24 hrs prior to transfection. For 150 mm plates ~6.0×$10^6$ 293, 293T or ΦNX-A cells were seeded.

Cells were ~60% confluent at the time of transfection. For 100 mm plates, ~10 µg DNA, ~438 µl H2O (depending on volume of DNA), 61 µl 2M $CaCl_2$ (total volume of $H_2O$/DNA/$CaCl_2$ mixture: 500 µl) was mixed in a microfuge tube. $CaCl_2$ was not added until the precipiates were ready to be prepared. For 150 mm plates, 30 µg DNA, ~878 µl H2O (depending on volume of DNA), 122 µl 2M $CaCl_2$ (total volume of $H_2O$/DNA/$CaCl_2$ mixture: 1000 µl) was used.

Lentiviral Production

For lentiviral production in 293 or 293T cells by Triple DNA co-transfection or to VSVg coat moloney viruses, using 100 mm plates, ~10 µg of three DNAs consisting of 5 µg of transfer vector, 3-4 µg of structural protein vector and 1-2 µg of pCI(VSVg) envelope vector was used. For 150 mm plates, ~30 µg of three DNAs (16 µg of lenti-transfer vector, 12 µg of Δ8.2 structural vector and 3 µg of pCI(VSVg) envelope vector). If the transfer vector does not have a GFP gene a GFP expression vector was usually included as ~5% of the total DNA, to know that the relative efficiency of the transfection (at the time of viral harvesting).

500 µl of 2×HBS (50 mM Hepes, 10 mM KCl, 12 mM Dextrose, 280 mM NaCl, 1.5 mM $Na_2HPO_4 \times 7H_2O$) was added to the $H_2O$/DNA/$CaCl_2$ mixtures (100 mm plates) or 1000 µl (for 150 mm plates) with constant bubbling of the latter mixtures in either microcentrifuge tubes (if precipitates are 0.5 ml of less) or 14 ml polypropylene tubes (if precipitates are 1-3 ml each) or into 15 ml polypropylene tubes. Then the $CaCl_2$ to the $H_2O$/DNA mixtures were added but to no more than four tubes at a time. The precipitates were then left at room temperature for 0-10 min.

Cells were in 9 ml of media (100 mm plates) or 18 ml media (150 mm plates). Excess media was removed leaving appropriate volumes in each size plate. Chloroquine was added to each plate to a final concentration of 25 µM.

The 1 ml $H_2O$/DNA/$CaCl_2$/2×HBS precipitates were gently added to the cells. Microscopic examination should reveal very fine black particles.

Plates were put in a 37° C., 5% $CO_2$ incubator. To ensure that the precipitates were evenly distributed plates were swirled gently by hand ~two times over the first 20-30 min of incubation.

5-8 hrs post-transfection the media was changed with 10 ml fresh GM (DMEM, 1% Penn/Step, 1% glutamine, 10% FBS) for 100 mm plates and 22 ml for 150 mm plates. 293 cells are more sensitive to chloroquine than ΦNX cells so the media was changed no longer than 5-7 hr post-transfection.

24 hrs post-transfection the GM was changed to 6.5-7 ml for the viral harvest (100 mm plates) or 16-17 ml (150 mm plates). 6 hours prior to harvesting plates were moved to a 32° C., 5% $CO_2$ incubator. The supernatants were centrifuged at 2000 RPM for 5 minutes to remove any cellular debris or were filtered thru a 0.45 micron filter.

Moloney and Lenti Retroviral Infections (Spinoculation Protocol)

To boost viral infection, adherent and suspension cells in tissue culture plate carriers can be spin infected at 2000-2400 RPM for 45-60 minutes at 30-32° C. Cells were infected at a high MOI with undiluted virus in 12, 24 or 6 well plates (generally using no more than 50-100×$10^3$ cells per well of a 6 well plate) in the presence of 8 µg/ml of polybrine. The cells were infected with 0.5-1.0 ml of viral supernatant per well of a 24 well plate, 1 ml per well of a 12 well plate and 2.0 ml/well of a 6 well plate. Viral supernatants from −80° C. freezer were thawed at room temperature and then added to cells along with the polybrine. For suspension cells, a counted number of cells were resuspended directly in the undiluted viral supernatant. The plate was sealed with parafilm all around to avoid evaporation and pH changes in the media during the spinoculation. After the first 'Spinoculation' the parafilm is removed from the plates and the viral supernatants are replaced with a fresh aliquot of virus and polybrine (thawed virus can be kept at room temperature during the first 45 minute spin) for a second equivalent spin or even a third spin (depending on the tolerance of the cells to centrifugation). For most cells, cells were usually spun twice (45 min each spin). For suspension cells, an additional equal volume of fresh viral supernatant was added to each well for a second spin. The parafilm was removed from the plates and without removing the viral supernatant, and continued to incubate at 32° C. in a $CO_2$ incubator for up to a total of 4-6 hr from the time of the first spinoculation (if three spins of 45 min. each was performed, the incubation with the last aliquot of virus was performed for another 2-3 hrs at 32° C.). The regular growth media was changed and the cells were incubated at 37° C. for 2 days prior to examining cells for GFP fluorescence. Drug selections were commenced 48 hrs post infection. If cells overgrew before reaching 48 hr, they were divided into more wells with regular growth media.

Example 4

LOXL2 shRNA Decreases Primary Tumor Development

Five million MDA-MB-231 cells were infected with control shRNA encoding lentiviruses or with lentiviral vector expressing the 195 LOXL2 directed shRNA, shR-NA.Loxl2.195 (si-LOXL2). Infected cells were selected prior to the injection with puromycin (2 micrograms/ml). Two days before injection, LOXL2 expression was determined in control vs shRNA.Loxl2.195 infected cells and the inhibition was about 65% based upon densitometry of Western blot (direct reading of fluorescence from the blot). The rate of proliferation of control vs shRNA.Loxl2.195 infected cells in vitro was similar. The infected cells were injected into the mammary fat pads of balb/c nu/nu female mice. Tumor volume was measured 6, 11, 14, 18, 22, 25, and 27 days after injection. (FIG. 8A) Tumor development was decreased in mice injected with MDA-231 si-control compared to mice injected with MDA-231 si-Loxl2 cells. (FIGS. 8A, B)

Example 5

Genes in MCF7 Cells Affected by LOXL2 Overexpression or Inhibition

Figures 9A, 9B:
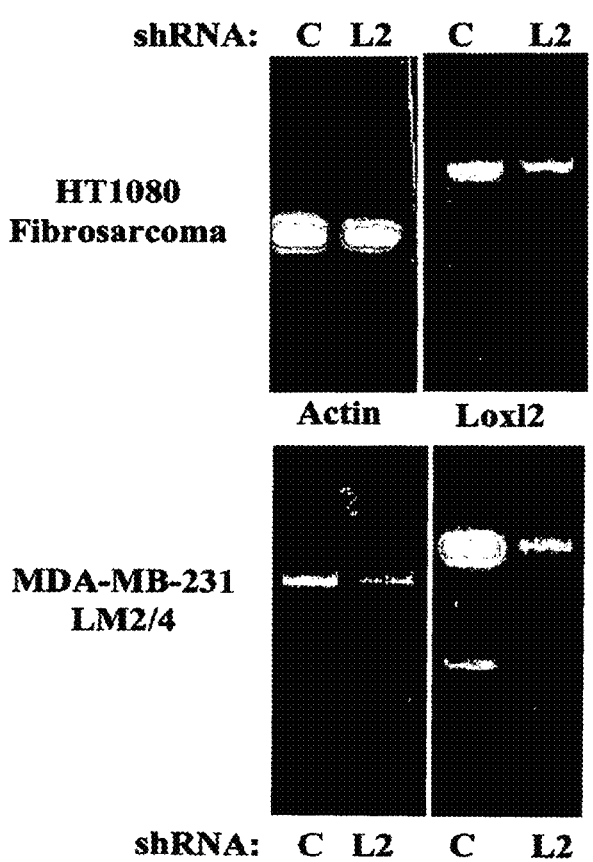
FIG. 9 illustrates genes in cancer cells affected by LOXL2 overexpression or inhibition of Loxl2 expression. (A) Genes upregulated in MCF-7 cells overexpressing recombinant LOXL2. Gene expression was measured by RT-PCR and Western blotting. Cells were transfected with a tetracycline-regulated construct expressing LOXL2 (clones 12 and 14), control lentiviral vector containing a non-related shRNA (WT), or a mutant of LOXL2 that is enzymatically inactive due to a mutation in its LTQ motif (Y689F). (B) Infection with lentivirus directed expression of shRNA directed against Loxl2. C=control shRNA, L2=sh.Loxl2.195

MCF7 cells were transfected with expression vector to overexpress LOXL2 (clone 12 and 14), infected with control lentiviral vector containing a non-related shRNA (WT), or infected with a mutant of LOXL2 that is enzymatically inactive due to a mutation in its LTQ motif (Y689F). Gene expression was measured by RT-PCR and Western blotting. RT-PCR was performed using standard protocols. Increase in expression was identified in a number of genes when LOXL2 was overexpressed (FIG. 9A)

Cells were infected with lentiviral shRNA vector 195. Cells were selected with puromycin and LOXL2 expression monitored by Western blot. RNA was isolated and RT-PCR was performed. PCR conditions using LOXL2 specific primers was 30 cycles of 55, 72, 95° C., 1 min. each (FIG. 9B)

Example 6

LOXL2 Expression is Enhanced by Hypoxia

Figure 10A:
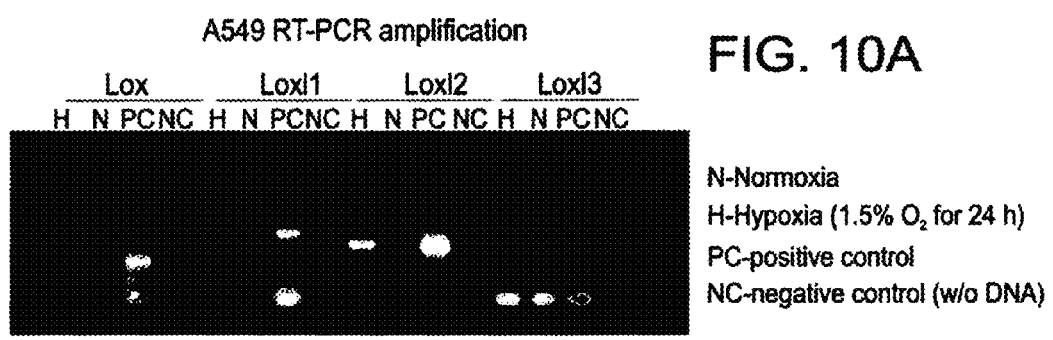
FIG. 10 illustrates expression of LOXL2 is enhanced by hypoxia. (A) Cells were incubated in a hypoxia chamber. Control was incubated in normoxic conditions (regular incubator). RNA was prepared from the cells at the end of the experiment and amplified by RT-PCR. PC=cells expressing recombinant LOXL2, NC=PCR without RT. (B) LOXL2 levels were assessed by Western blot. Cells were stimulated for the indicated times with the indicated concentration of $CoCl_2$. Equal concentrations of cell lysates were prepared with lysis buffer. Cell lysates were separated on a gradient SDS/PAGE gel, blotted and probed with our anti-LOXL2 antibodies. Membranes were stripped and reprobed with an antibody directed against β-actin to verify equal loading.
Figure 10B:
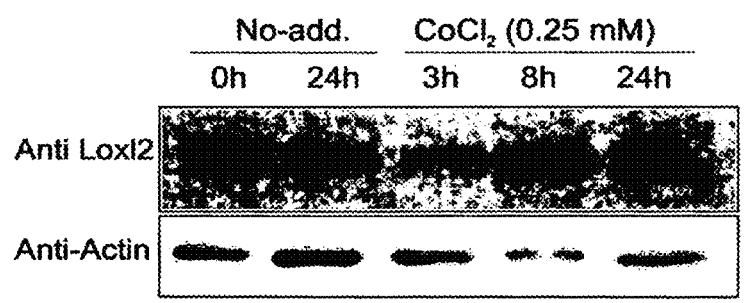

Cells were incubated in a hypoxia chamber at 37° C. at 1.5% $O_2$ for 24 h. A control was incubated in normoxic conditions (regular incubator). RNA was prepared from the A549 cells and amplified by RT-PCR (30 cycles of 55, 72, 95° C., 1 min. each). LOXL2 expression is increased under hypoxic conditions (FIG. 10A)

LOXL2 levels were assessed by Western blot. Cells were stimulated for the indicated times with the indicated concentration of $CoCl_2$ (FIG. 10B) Equal concentrations of cell lysate was prepared with lysis buffer containing 0.1% DOC and 1% NP40 with protease inhibitors and 10 mM Hepes buffer, pH-7.2. Cell lysates were separated on an 8%-10% gradient SDS/PAGE gel, blotted and probed with anti-LOXL2 antibodies. Membranes were stripped and reprobed with an antibody directed against β-actin to verify equal loading.

Example 7

Human Umbilical Vein Derived Endothelial Cells Contain Cell Surface Bound LOXL2 Receptor Four different cell lines, HUVEC, LE2, HMEC, and Balb, were tested for their specific binding to LOXL2 by measuring using iodinated LOXL2. LOXL2 was iodinated and added to each well at a final concentration of 0.35 µg/ml. Competition was done with unlabeled LOXL2 (3.5 µg/ml) (FIG. 11A).

Wells were coated with gelatin, laminin or fibronectin to test for their ability to bind LOXL12. LOXL2 was iodinated and added to each well at a final concentration of 0.35 µg/ml. Competition was done with unlabeled LOXL2 (3.5 µg/ml). No specific binding was determined (FIG. 11B) indicating binding observed in FIG. 11A was not caused by binding to these ECM components.

Figure 11A:
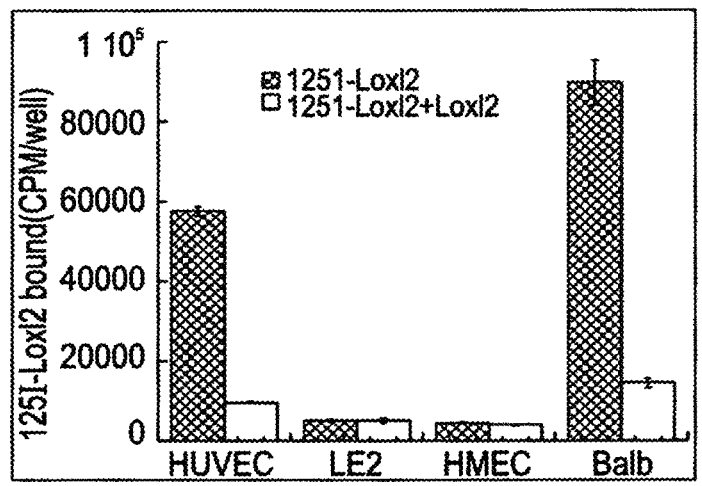
FIG. 11 illustrates expression of a cell surface bound LOXL2 receptor in human umbilical vein derived endothelial cells (HUVEC). (A) LOXL2 was iodinated and four different cell lines were tested for their specific binding to LOXL2. Iodinated LOXL2 was added to each well and competition was done with unlabeled LOXL2. (B) LOXL2 does not bind specifically to gelatin, laminin or fibronectin. Iodinated LOXL2 was added to each well and competition was done with unlabeled LOXL2. There was no specific binding demonstrating the binding observed to the cells is not caused by binding to the ECM components fibronectin, laminin, or gelatin. (C) Iodinated LOXL2 was added to each well and competition was done with unlabeled LOXL2. In the absence or addition of 100 ug/ml heparin (heparin does not inhibit the binding) or after prior digestion with heparinase (does not affect the binding to the putative receptor).
Figure 11B:
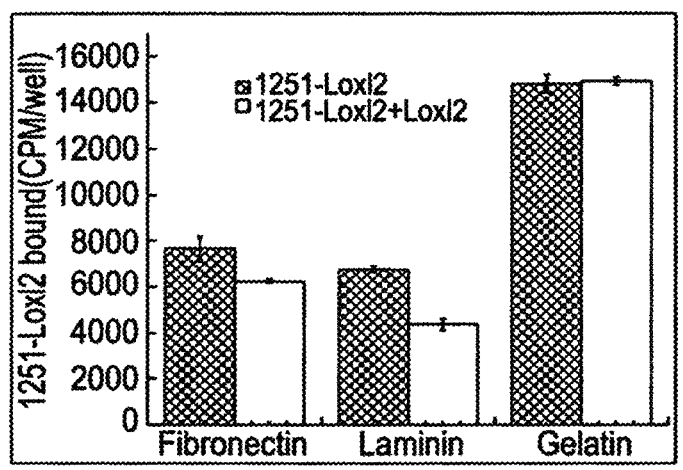
Figure 11C:
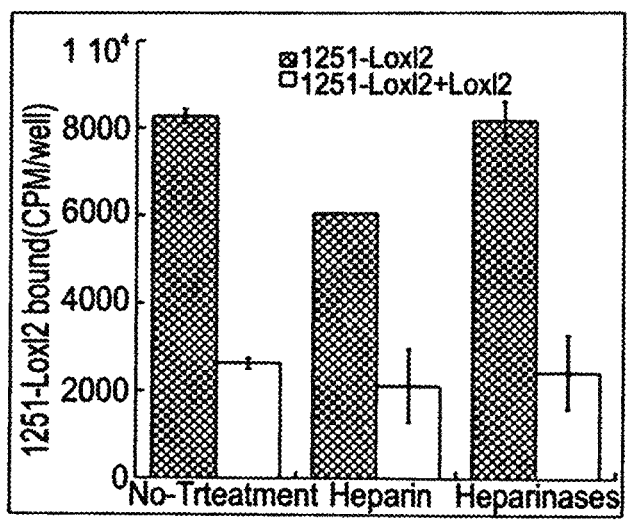

The same binding conditions as described in FIG. 11A above but in the absence or addition of 100 ug/ml heparin or after prior digestion with heparinase. Neither absence nor addition of heparin of binding affects LOXL2 binding. (FIG. 11C).

Example 8

LOXL2 and LOXL3 are Expressed in Neuronal Cells

Formalin fixed paraffin embedded 5 um sections from normal brain cortex were examined by in situ hybridization. (FIG. 12)

Preparation of DIG-Labeled RNA Probe

Digoxygenine (DIG-11-UTP)-labeled RNA probes were prepared in either sense or antisense orientation. The probes were synthesized by run-off in vitro transcription using T7 RNA polymerase and the Dig/Genius RNA labeling kit (Roche Boheringer-Manheim). Probes were generated by PCR reaction from human LOX, LOXL1, LOXL2, and LOXL3 cDNAs corresponding to nucleotides (starting from the first ATG) 164-560 for LOX, 668-1093 for LOXL1, 403-1102 for LOXL2, and 479-1913 for LOXL3. The primers were specific for each probe and carried restriction enzymes for cloning to the pBluescript (KS, SK) vector. The primers were:

hLOX: 5' (EcoRI) CGCCGGAATTCGCTCACAGTAC-CAGCCTCAG

3' (PstI) CCAAAACTGCAGGTAGTAGTTG-TAATAAGGGT hLOXL1: 5' (EcoRI) CGCCGGAATTCGGTCATCTAC-CCCTACCAGC

3' (XbaI) CTAGTCTAGAACATAGTTGGGGTCTGG-GAC hLOXL2: LOXL2/pCDNA3.1 hygro was digested with EcoRA-NotI and fragment was cloned hLOXL3: LOXL3/pCDNA3.1 hygro was digested with Xho-BglII and fragment was cloned.

The fragments were cloned into pBluescript in "KS" or "SK" orientation in order to generate "sense" or "antisense" probes.

The reaction mixture for problem labeling contained: 1 ug of DNA (LOXL2, LOX, LOXL1, or LOXL3 in pBluescript), 10× reaction buffer (Boehringer-Mannheim T7-RNA polymerase kit), 100 mM DTT (Sigma), 10× Dig-labeled dNTPs (Boehringer-Mannheim, Cat. No. 1175025), RNAse inhibitor (Promega, 15 units per reaction), 10× T7-RNA polymerase, and DEPC (diethyl pyrocarbonate)-treated water to complete volume of 20 ul. The reaction was for 2 hours at 37° C.

The reaction was stopped by addition of 0.8 ul EDTA. The Dig-labeled RNA probe was then precipitated by the addition of 1 µl of 20 mg/ml glycogen, 2 ul 4M LiCl, and 55 ul chilled ethanol. The solution was mixed well and incubated overnight at −70° C. The probe was pelleted by centrifugation for 15 minutes at 4° C. at 13000 g. The precipitate was washed with cold 70% ethanol and spun again for 5 minutes at 4° C. at 13000 g. The pellet was dried and resuspended in 100 ul DEPC treated DDW (distilled deionized water). Four µl of probe was separated on regulated 1% TAE agarose gel with 0.005% ethidium bromide to determine RNA probe formation. Final probe concentration for hybridization was 1 ug/ml.

Pre-Treatment of Slides

Formaline-fixed paraffin-embedded 5 um tissue sections were deparaffinized by three washes of 5-10 min. each with 100% xylene. The sections were rehydrated through a series of 100%, 95%, 70%, and 30% ethanol washes (5 min. incubation in each solution) at room temperature. The slides were then washed twice with DEPC treated water for 2 min. and then treated with 0.2M HCl for 10 min to denature proteins. The sections were then washed twice with PBS and washed twice with water and subsequently digested with Proteinase-K (20 ug/ml in TE, 10 min at room temperature). The reaction was stopped by two washes with DEPC treated water. The slides were then washed twice with PBS for 2 min.

Hybridization

Pre-hybridization was performed by incubation of slides for 2 hours at 45° C. with preheated (at 70° C.) hybridization solution (see below). The probe was diluted in the preheated hybridization solution to a final concentration of 1 µg/ml and denatured by incubation at 80° C. for 5 min and was chilled for 3 min in ice prior to addition to the slides. The slides were dried and the probes were added to the slides. The sections were covered with parafilm and incubated in a humidified chamber overnight at 45° C.

Post-Hybridization Washes and Incubation with Anti DIG Antibody

The slides were washed briefly with 2×SSPE at room temperature for 5 min. and then incubated with 0.2×SSPE at 50-55° C. for 1 hour. The slides were then washed by additional incubation with 0.2×SSPE at 50-55° C. for 1 hour and cooled to room temperature. After washing with PBS for 5 min. at room temperature, the slides were incubated with Buffer 2 (see below) for 45 min. at room temperature with gentle agitation. The slides were washed with BSA wash solution for 45 min. at room temperature with gentle shaking.

The anti-DIG antibody was diluted to final concentration of 1:1000-1:1500 in Buffer 2 and added to the slides (~150 ul/slide). The slides were covered with parafilm and incubated in a humidified chamber overnight at 4° C.

The slides were then washed three times with BSA wash solution, for 5 min. each wash. The slides were then washed with Buffer 2 for 30 min at room temperature with gentle agitation.

Detection of Bound Anti-DIG Antibodies

The slides were incubated in Buffer 3 (see below) for 2 min. at room temperature without shaking. For colorimetric detection, 3 ul BCIP and 4.2 ul NBT were diluted in 2 ml of Buffer 3. The solution was added to the slides and incubated in the dark at room temperature for required time. The reaction was stopped by addition of Stop Buffer (see below). The slides were then washed with DDW and counter stained with Mayers Hematoxylin (1:10 in DDW for 5-7 sec). Finally the slides were washed with DDW and mounted with Mount Q and covered with coverslips.

Solutions

All solutions were prepared in DEPC treated water (0.1% DEPC in DDW for 18 hours and then autoclaved).

Prehybridization Solution: 50% formamide, 100 mM Tris (pH 7.6), 150 ug/ml tRNA, 1 mg/ml yeast total RNA, 10% Dextran sulfate, 300 mM NaCl, 1 mM EDTA, 1% blocking reagent)

BSA Wash Solution: 1% BSA, 0.3% Triton X-100, 100 mM Tris (pH 7.6), 150 mM NaCl.

Buffer 1: 100 mM Tris (pH 7.6), 150 mM NaCl
Buffer 2: blocking reagent diluted to 2% in Buffer 1
Buffer 3: 100 mM Tris (pH 9.5), 100 mM NaCl, 50 mM $MgCl_2$ Stop Buffer: 100 mM Tris (pH 8.0), 1 mM EDTA
"GVA-Mount solution" from Zymed (Cat. No. 00-8000)

Although the present disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for inhibiting fibrosis, tumor growth, or tumor metastasis, in a subject, the method comprising: administering a polynucleotide to the subject, thereby inhibiting fibrosis, tumor growth, or tumor metastasis, wherein the tumor is breast adenocarcinoma, fibrosarcoma or melanoma, wherein the polynucleotide comprises:

a first sequence comprising a nucleic acid sequence of SEQ ID NO: 20 or SEQ ID NO: 21, a second sequence comprising a region of complementarity to the nucleic acid sequence of SEQ ID NO: 20 or SEQ ID NO: 21, wherein the region of complementarity is at least 19 bases in length, and a linking sequence that joins the first sequence to the second sequence, wherein the polynucleotide forms a hairpin-loop structure having a double-stranded stem region of between 19 and 21 base pairs in length that comprises the region of complementarity, wherein ends of the double-stranded stem region are connected by the linking sequence.

2. The method of claim 1, wherein the first sequence comprises the nucleic acid sequence of SEQ ID NO: 20.

3. The method of claim 2, wherein the first sequence is SEQ ID NO: 20.

4. The method of claim 2, wherein the second sequence comprises the complement of SEQ ID NO: 20.

5. The method of claim 1, wherein the first sequence comprises the nucleic acid sequence of SEQ ID NO: 21.

6. The method of claim 5, wherein the first sequence is SEQ ID NO: 21.

7. The method of claim 5, wherein the second sequence comprises the complement of SEQ ID NO: 21.

8. The method of claim 1, wherein the polynucleotide is at least twice the length of SEQ ID NO: 20.

9. The method of claim 1, wherein the linking sequence is between 4 and 30 bases in length.

10. The method of claim 3, wherein the second sequence is the complement of SEQ ID NO: 20.

11. The method of claim 6, wherein the second sequence is the complement of SEQ ID NO: 21.

12. The method of claim 1, wherein the linking sequence is between 4 and 23 base pairs in length.

\* \* \* \* \*